US009074202B2

(12) United States Patent
Bienz et al.

(10) Patent No.: US 9,074,202 B2
(45) Date of Patent: Jul. 7, 2015

(54) METHOD OF INHIBITING HUMAN TRABID

(75) Inventors: Mariann Bienz, Cambridge (GB); Felix Randow, Cambridge (GB); Hoanh Tran, South San Francisco, CA (US); Thomas Schwarz-Romond, Bammental (DE)

(73) Assignee: MEDICAL RESEARCH COUNCIL, Wiltshire (GB)

(*) Notice: Subject to any disclaimer, the term of this patent is extended or adjusted under 35 U.S.C. 154(b) by 817 days.

(21) Appl. No.: 12/302,317

(22) PCT Filed: May 21, 2007

(86) PCT No.: PCT/GB2007/001839
§ 371 (c)(1),
(2), (4) Date: Nov. 25, 2008

(87) PCT Pub. No.: WO2007/138253
PCT Pub. Date: Dec. 6, 2007

(65) Prior Publication Data
US 2009/0275635 A1 Nov. 5, 2009

(30) Foreign Application Priority Data
May 26, 2006 (GB) .................................. 0610542.3

(51) Int. Cl.
C07H 21/04 (2006.01)
C12N 9/64 (2006.01)
C12N 15/11 (2006.01)
C12N 15/113 (2010.01)

(52) U.S. Cl.
CPC ............ *C12N 9/6421* (2013.01); *C12N 15/111* (2013.01); *C12N 15/1137* (2013.01); *C12N 2310/14* (2013.01); *C12N 2320/10* (2013.01)

(58) Field of Classification Search
CPC .......................... C12N 15/111; C12N 2310/141
See application file for complete search history.

(56) References Cited

U.S. PATENT DOCUMENTS

2004/0023908 A1* 2/2004 Bennett et al. ................... 514/44
2004/0259247 A1* 12/2004 Tuschl et al. ................... 435/375
2008/0108583 A1* 5/2008 Feinstein .......................... 514/44

FOREIGN PATENT DOCUMENTS

WO 2004/005457 A 1/2004
WO 2004/011636 A 2/2004

OTHER PUBLICATIONS

Evans, P. C. et al., Biochemical Journal, 357(3):617-623 (2001). "Isolation and Characterization of Two Novel A20-Like Proteins."
Evans, P.C. et al., Journal of Biological Chemistry, 278(25):23180-23186 (2003). "A Novel Type of Deubiquinating Enzyme."

Alam, S.L. et al., EMBO J. 23, 1411-1421 (2004). "Ubiquitin Interactions of NXF Zinc Fingers."
Balakirev, M.Y. et al EMBO 4(5), 517-522 (2003). Otubains: A new family of cysteine proteases in the ubiquitin pathway.
Evans, P.C. et al., Biochem. J.; 357: 617-623 (2001). "Isolation and Characterization of Two Novel A20-Like Proteins."
Evans, P.C. et al., J. Biol. Chem. 278:23180-23186 (2003). "A Novel Type of Deubiquitnating Enzyme."
Hendriksen, J. et al. J Cell Biol 171, 785-797 (2005). "RanBP3 enhances nuclear export of active B-catenin independently of CRM1."
Kanayama, et al., Mol. Cell, 15(4), 535-548 (2004). "TAB2 and TAB3 Activate the NF-kB Pathway through Binding to Polyubiquitin Chains."
Korinek, V. et al., Science 275, 1784-1787 (1997). "Constitutive Transcriptional Activation by a B-Catenin-Tcf Complex in APC-/-Colon Carcinoma."
Kramps, T. et al. Cell 109, 47-60. (2002). "Wnt/Wingless Signaling Requires BCL9/Legless-Mediated Recruitment of Pygopus to the Nuclear B-Catenin-TCF Complex."
Liu, F. et al. Development 132, 5375-85 (2005). "Distinct roles for Xenopus Tcf/Lef genes in mediating specific responses to Wnt/B-catenin signalling in mesoderm development."
Makarova, K. S. et al. Trends Biochem Sci 25, 50-52 (2000). "A novel superfamily of predicted cysteine proteases from eukaryotes, viruses and *Chlamydia pneumoniae*."
Morin, P.J. et al., Science 275, 1787-1790 (1997). "Activation of B-Catenin-Tcf Signaling in Colon Cancer by Mutations in B-Catenin or APC."
Nanao, M. H. et al. EMBO Rep 5, 783-8 (2004). "Crystal structure of human otubain 2".
Sansom, O. J. et al. Genes Dev 18, 1385-90 (2004). "Loss of Apc in vivo immediately perturbs Wnt signaling, differentiation, and migration."
Sierra, J. et al. A. Genes Dev 20, 586-600 (2006). "The APC tumor suppressor counteracts B-catenin activation and H3K4 methylation at Wnt target genes."
Thompson, B et al. Nat Cell Biol. 4, 367-373 (2002). A new nuclear component of the Wnt signalling pathway.
Wang, B. et al., JBC 278, 20225-20234 (2003). "Structure and Ubiquitin Interactions of the Conserved Zinc Finger Domain of Npl4."

* cited by examiner

*Primary Examiner* — Jon E Angell
(74) *Attorney, Agent, or Firm* — Nixon Peabody LLP; Mark J. FitzGerald

(57) ABSTRACT

The invention provides a method of modulating Wnt signalling comprising modulating Trabid activity. Preferably modulating Trabid activity comprises inhibiting; Trabid activity. The invention also provides a method of reducing TCF transcription, said method comprising reducing Trabid activity. A method for identifying a-modulator of Trabid said method comprising; providing a Trabid substrate comprising a detectable moiety coupled to a tag moiety by ubiquitin; immobilizing first and second portions of said substrate; adding a candidate modulator to the first said portion; contacting first and second portions with Trabid; incubating to allow Trabid action, assaying cleavage of ubiquitin by separation of tag from detectable moiety, wherein separation of an amount of detectable moiety from said first portion which is different from the amount of detectable moiety separated from said second portion identifies said candidate as a modulator of Trabid. The invention provides uses of Trabid and of Trabid inhibitors as-medicaments.

4 Claims, 21 Drawing Sheets

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial
<220> FEATURE:
<223> OTHER INFORMATION: siRNA sequence

<400> SEQUENCE: 1
agaggtgtct caacaagca                                               19

<210> SEQ ID NO 2
<211> LENGTH: 19
<212> TYPE: DNA
<213> ORGANISM: Artificial
<220> FEATURE:
<223> OTHER INFORMATION: siRNA sequence

<400> SEQUENCE: 2
agaggcttct caataata                                                19

<210> SEQ ID NO 3
<211> LENGTH: 18
<212> TYPE: DNA
<213> ORGANISM: Artificial
<220> FEATURE:
<223> OTHER INFORMATION: siRNA sequence

<400> SEQUENCE: 3
ggcuucuuca auaauatt                                                18

<210> SEQ ID NO 4
<211> LENGTH: 21
<212> TYPE: DNA
<213> ORGANISM: Artificial
<220> FEATURE:
<223> OTHER INFORMATION: siRNA sequence

<400> SEQUENCE: 4
agaggugucu caacaagcat t                                            21

<210> SEQ ID NO 5
<211> LENGTH: 21
```

```
<212> TYPE: DNA
<213> ORGANISM: Artificial
<220> FEATURE:
<223> OTHER INFORMATION: siRNA sequence

<400> SEQUENCE: 5
gaaucuaucu gccuuuggat t                                              21

<210> SEQ ID NO 6
<211> LENGTH: 21
<212> TYPE: DNA
<213> ORGANISM: Artificial
<220> FEATURE:
<223> OTHER INFORMATION: siRNA sequence

<400> SEQUENCE: 6
agacuuccgc agcuucauat t                                              21
```

METHOD OF INHIBITING HUMAN TRABID

CROSS-REFERENCE TO RELATED APPLICATIONS

This application is a 371 National Stage of International Application No. PCT/GB2007/001839 filed on May 21, 2007, which designates the United States, and which claims the benefit under 35 U.S.C. §119(a) of Great Britain Application No. 0610542.3 filed on May 26, 2006, the entire contents of which are incorporated herein by reference.

FIELD OF THE INVENTION

The invention relates to the Wnt signalling pathway and to disorders associated with defects in that pathway. In particular the invention relates to adenomatous polyposis coli (APC) signalling and the amelioration or reduction in effectors thereof in the treatment of disorders such as colorectal cancer.

BACKGROUND TO THE INVENTION

Wnt signalling has been shown to be important in cancer. Indeed, Wnt signalling is implicated in tumour promotion and cancer via genetic defects at numerous levels or stages in the pathway. This topic is reviewed in detail by Polakis (2000 Genes and Development vol 14 pages 1837-1851).

Adenomatous polyposis coli (APC) has a central role in the Wnt signalling pathway. APC is an important tumour suppressor whose function is lost in the majority of sporadic and hereditary colorectal cancers. Its best understood function is the downregulation of β-catenin, a key effector of the Wnt signalling pathway. Moreover, APC proteins also appear to have a separate function in maintaining cadherin mediated cell adhesion, and loss of this function could accelerate the transition of tumours to invasive malignancy.

APC is inactivated in more than 80% of all colorectal cancers. The APC gene is defective in familial adenomatous polyposis (FAP), a dominantly-inherited disease that predisposes to colorectal tumours. Inactivation of APC is also seen in most sporadic tumours, and is an early, and possibly initiating, event in tumorigenesis.

APC is a negative regulator of the Wnt signalling pathway. It binds to and promotes the downregulation of β-catenin, a key effector of this pathway. In cells in which this pathway is inactive, β-catenin is rapidly degraded, as a result of phosphorylation in its N-terminus afforded by the Axin destruction complex that also contains glycogen synthase kinase 3β. On Wnt signalling, β-catenin is stabilised and translocates to the nucleus where it binds to TCF/LEF factors to activate the transcription of Wnt target genes. These changes in transcription are thought to be the basis for tumorigenesis. Thus it is a problem to control the transcription of Wnt target genes, or to attenuate their expression.

Current evidence suggests that APC, like β-catenin, may also have a separate function in cellular adhesion. This evidence arose from work in *Drosophila* where the APC relative E-APC is associated with adherens junctions in epithelia and appears to affect cellular adhesion. Evidence is emerging that this also applies to human cells: the APC tumour suppressor is associated with adhesive lateral membranes in various polarised mammalian cells, and has been implicated in the exchange of β-catenin at adherens junctions and in cellular adhesion of colorectal cancer cells. These findings are potentially relevant with regard to tumor progression since loss of cadherin-mediated adhesion often accompanies the transition of benign tumours to invasive carcinomas. Thus, it is problem to promote or maintain cellular adhesion such as cadherin-mediated adhesion.

The most conserved domain of APC proteins is their N-terminal Armadillo Repeat Domain (ARD), a putative protein-interaction domain. The closest relatives of this domain are found in β-catenin and α-importin, the functions and structures of these ARDs are well known, including their precise molecular interactions with many of their functionally relevant ligands. By contrast, it is a problem in the art that the molecular function of the ARD of APC proteins is poorly understood, and although there have been reports of putative ligands, their functional relevance with regard to APC is still unclear or unknown.

The present invention seeks to overcome problem(s) associated with the prior art.

SUMMARY OF THE INVENTION

The present inventors have discovered a new protein which interacts in a biologically meaningful way with the APC protein. This protein has been isolated on the basis of its ability to interact with the wild type protein but not with a specific ARD repeat mutant APC protein. The protein identified is Trabid. Trabid protein does not have any biological function disclosed in the prior art. Thus, a completely new and biologically important signalling role has been ascribed to this protein by the present work.

Furthermore, Trabid has been biochemically characterised. Trabid has been identified as a new deubiquitylase enzyme. The ubiquitin binding domain has been defined and experimentally demonstrated. Trabid has binding specificity for K63-linked ubiquitin, which has been defined and experimentally demonstrated. This activity is required for Wnt pathway activity in colorectal cancer or Wnt-stimulated cells. The deubiquitylase activity has been defined and experimentally demonstrated. Furthermore, the effects of manipulation of Trabid (particularly inhibition and/or depletion) and the use of Trabid inhibitors have been shown to encompass modulation of biologically important Wnt effectors in human cell lines with activated Wnt signalling, as well as in colorectal cell lines. Thus, a functional link between Trabid and Wnt signalling/TCF-mediated transcription has been established for the first time.

The invention is based on these remarkable findings.

Thus the invention provides a method of modulating Wnt signalling comprising modulating Trabid activity. Preferably modulating Trabid activity comprises inhibiting Trabid activity.

In another aspect, the invention provides a method of reducing TCF transcription, said method comprising reducing Trabid activity. Preferably Trabid activity is reduced using siRNA to Trabid or using dominant negative Trabid. When using dominant negative Trabid, this is introduced into the system in which it is desired to reduce Trabid activity, for example by supply of dominant negative Trabid polypeptide, or by expression from a nucleic acid encoding same (i.e. by introduction of said nucleic acid into said system by any suitable means known in the art). Preferably said TCF expression is not β-catenin-Lef fusion stimulated transcription. Preferably said TCF transcription is Dv1-stimulated, Wnt3A stimulated, LiCl stimulated, or mβ-TrCp-ΔF stimulated TCF transcription. Preferably said TCF transcription is Dv1-stimulated TCF transcription. Preferably said TCF activity is TCF activity stimulated by APC mutation or loss and/or by beta-catenin activation. These specific applications are demonstrated in the examples section, e.g. with reference to the APC-mutant cancer cell line SW480, and the beta-catenin mutant cancer cell line HCT116 (as shown in the figures), both of which depend on Trabid activity.

In another aspect, the invention relates to a method of inhibition of TCF transcription comprising inhibition or downregulation of Trabid.

In another aspect, the invention provides a method of treating familial adenomatous polyposis in a subject comprising modulating Trabid signalling in said subject.

In another aspect, the invention provides a method of treating colorectal cancer in a subject comprising modulating Trabid signalling in said subject. References to colorectal cancer suitably include colon cancer.

Preferably Trabid modulation is Trabid inhibition.

In another aspect, the invention provides use of Trabid in deubiquitylation, preferably use of Trabid to remove a ubiquitin moiety from a polypeptide, preferably use of Trabid in the deubiquitylation of a polypeptide.

Deubiquitylation means removal of one or more ubiquitin units from a polypeptide comprising same. Depending upon where cleavage for removal takes place, the units released may correspond to complete ubiquitin units, polyubiquitin chains, or fragments of ubiquitin. Preferably complete ubiquitin units are released. Preferably deubiquitylation means the complete removal of ubiquitin from a polypeptide, and preferably means removing all ubiquitin group(s) from said polypeptide.

Preferably the deubiquitylation comprises cleavage of K63-linked ubiquitin. Preferably Trabid comprises at least the C-terminal ovarian tumour (OTU) domain. Preferably Trabid comprises the N-terminal NZF finger motifs. (Zinc finger motifs are classified into a number of different types. Trabid has NZF-type fingers, which are also known as 'RanBP-type fingers', and as 'ZnF_RBZ fingers'—the terms are used interchangeably herein.)

Preferably Trabid comprises full length human Trabid polypeptide.

In another aspect, the invention provides Trabid inhibitor for use as a medicament.

In another aspect, the invention provides use of Trabid inhibitor for the manufacture of a medicament for colorectal cancer.

In another aspect, the invention provides use of Trabid inhibitor for the manufacture of a medicament for familial adenomatous polyposis.

In another aspect, the invention provides a Trabid inhibitor for use in the treatment of colorectal cancer.

In another aspect, the invention provides a Trabid inhibitor for use in the treatment of familial adenomatous polyposis.

Preferably said Trabid inhibitor is siRNA to Trabid, or is a dominant negative Trabid such as Trabid C443S. Suitably the Trabid inhibitor may be an inhibitor of deubiquitinase activity such as ubiquitin aldehyde. Suitably the Trabid inhibitor may be an inhibitor of K63 linked ubiquitin binding activity.

In another aspect, the invention provides use of Trabid in the precipitation of a polypeptide comprising ubiquitin such as K63 linked ubiquitin. This is a useful reagent for example in immunoprecipitation, or preparation of immobilised APC (or other components) by virtue of its ability to bind Trabid.

In another aspect, the invention provides use of Trabid in the modulation of β-catenin. In particular, the invention provides use of Trabid in the modulation of transcriptional activity of β-catenin by Trabid. Preferably said use acts in modulation off transcriptional activity of β-catenin rather than mere stabilisation of β-catenin. In another aspect, the invention provides use of Trabid in the modulation of cell adhesion. Preferably said modulation of cell adhesion is cadherin-modulated cell adhesion.

In another aspect, the invention provides use of Trabid in the maintenance or stimulation of TCF transcription.

In another aspect, the invention provides a method of decreasing nuclear TCF3 and/or TCF4 by reducing Trabid activity.

In another aspect, the invention provides a method for identifying a modulator of Trabid said method comprising; providing a Trabid substrate comprising a detectable moiety coupled to a tag moiety by ubiquitin; immobilising first and second portions of said substrate; adding a candidate modulator to the first said portion; contacting said first and second portions with Trabid; incubating to allow Trabid action, and assaying cleavage of the ubiquitin by separation of the tag from the detectable moiety, wherein separation of an amount of detectable moiety from said first portion which is different from the amount of detectable moiety separated from said second portion identifies said candidate as a modulator of Trabid.

Trabid means the Trabid polypeptide or nucleic acid encoding same. Preferably Trabid refers to the polypeptide. Preferably Trabid polypeptide comprises the Trabid deubiquitylase active domain. This is described in more detail below.

Trabid is disclosed for the first time to have deubiquitylase activity, and to be involved in Wnt signalling. Thus in a broad aspect the invention relates to a method for the identification of modulators of Wnt signalling, said method comprising assaying Trabid deubiquitylase activity in the presence and absence of a candidate modulator, wherein a difference in deubiquitylase activity between the presence and absence of the candidate modulator identifies it as a modulator of Wnt signalling. In another aspect, the invention provides a method for the identification of modulators of Trabid, said method comprising assaying Trabid deubiquitylase activity in the presence and absence of a candidate modulator, wherein a difference in deubiquitylase activity between the presence and absence of the candidate modulator identifies it as a modulator of Trabid. Preferably said candidate modulators are candidate inhibitors, and a reduction in Trabid activity in the presence of said candidate inhibitor identifies it as an inhibitor of Wnt signalling and/or Trabid.

The candidate modulator may be any entity such as a chemical entity, biological macromolecule or other such substance.

Preferably said method of identifying a modulator further comprises the step of manufacturing an effective amount of said modulator.

Preferably said method of identifying a modulator further comprises the step of formulating said modulator for administration to a subject.

Preferably said method of identifying a modulator further comprises the step of manufacturing a medicament comprising said modulator.

Preferably separation of the tag from the detectable moiety is determined by assaying for release of the detectable moiety into the supernatant. In this way the supernatant advantageously possesses the readout signal. In another embodiment, preferably separation of the tag from the detectable moiety is determined by assaying for retention of the detectable moiety in the immobilised material. In this way the washed immobilised vessel may be scanned for the readout.

Preferably said first and second portions of said substrate are immobilized via the tag moiety.

The tag moiety and the detectable moiety may each be a 'tag' if desired. The key point is that they can preferably be distinguished. This feature will typically mean that the tag moiety and the detectable moiety are different, since if they were the same then it would be potentially difficult to readout or control the assay. If the tag moiety and the detectable moiety are the same then the assay readout will rely on separation of the supernatant from the assay vessel for separate handling, which can add labour to the working of the assay.

Preferably the tag moiety and the detectable moiety are different. In this embodiment the tag moiety can advantageously be anything suitable for immobilisation (and therefore does not need to be detectable), potentially giving greater choice and/or reducing the cost of the assay materials.

Preferably the amount of Trabid in each treatment is the same.

Preferably separation of a lower amount of detectable moiety from said first portion compared to said second portion identifies said candidate modulator as an inhibitor of Trabid. Release of a lower amount would be due to lower Trabid activity, thereby showing that inhibition had taken place.

In another embodiment, preferably separation of a higher amount of detectable moiety from said first portion compared to said second portion identifies said candidate modulator as an activator of Trabid. If the candidate modulator activates Trabid then for a given reaction time (incubation time) then a greater quantity of substrate will have been digested, giving a greater readout.

Preferably said Trabid substrate comprises a GST-ubiquitin-ubiquitin-S fusion protein. wherein said detectable moiety comprises S, and wherein said tag moiety comprises GST.

Preferably said first and second portions of substrate are immobilised in separate wells of a microtitre plate. This is advantageously a convenient platform for high throughput screening.

Preferably immobilisation is by attachment to an anti-GST antibody which has been previously coated onto the inner surface of the wells of a microtitre plate.

In another aspect, the invention provides a method of modulating the armadillo repeat domain (ARD) of APC, said method comprising contacting said APC with Trabid. Preferably said modulation is by steric hindrance brought about by Trabid binding e.g. blocking of other protein binding to the ARD domain.

In another aspect, the invention provides a method of identifying a mutant Trabid which binds to mutant APC which method comprises providing candidate mutant Trabid polypeptide; contacting said candidate mutant Trabid polypeptides with said mutant APC polypeptide and monitoring association between said candidate mutant Trabid polypeptides and said mutant APC polypeptide, wherein association between said polypeptides indicates that the candidate mutant Trabid polypeptide binds said mutant APC. Preferably said mutant APC is N507K APC, or N175K E-APC.

In broad aspect, the invention relates to an APC polypeptide wherein said polypeptide comprises an N175 or N507 mutation. In one embodiment preferably said APC is human APC and said mutation comprises an N507 mutation, preferably said N507 mutation is N175. In another embodiment, preferably said APC is E-APC and said mutation comprises an N175 mutation, preferably said N175 mutation is N175K. Preferably the APC polypeptide as described above exhibits reduced capacity to bind Trabid relative to the wild type APC polypeptide. Preferably the invention relates to uses of this APC polypeptide in modulation of Wnt signalling.

The candidate mutant Trabid polypeptide may be a library of multiple candidate mutant Trabid polypeptides. Preferably said library is an expression library which produces said candidate mutant Trabid polypeptides from nucleic acid(s) encoding same.

In another aspect, the invention provides Trabid or a fragment thereof wherein said Trabid comprises a C443 mutation. Preferably said Trabid is human Trabid comprising amino acid sequence of accession number CAB64449 wherein said C443 mutation is C443S. In another aspect, the invention provides a nucleic acid encoding a Trabid or fragment thereof as described above.

In another aspect, the invention provides Trabid for use as a medicament. In another aspect, the invention provides use of Trabid for the manufacture of a medicament for colorectal cancer.

In another aspect, the invention provides use of Trabid for the manufacture of a medicament for familial adenomatous polyposis.

In another aspect, the invention provides Trabid for use in the treatment of colorectal cancer.

In another aspect, the invention provides Trabid for use in the treatment of familial adenomatous polyposis.

In another aspect, the invention provides Trabid for use in the maintenance of stem cell compartments and/or stimulation of stem cell activity.

In another aspect, the invention provides use of recombinant or purified Trabid as an E3 ubiquitin ligase.

DETAILED DESCRIPTION OF THE INVENTION

The invention relates to studying and enhancing the understanding of the functions of APC ARD domain interacting proteins, such as Trabid, and to examining their putative roles as regulators or effectors of APC, and/or their effects on Wnt signalling and cell adhesion. The invention thus enables better understanding of the APC tumour suppressor and its function not only in Wnt signalling, but also in cell adhesion. Furthermore, the invention enables identification of molecules and mechanisms that attenuate or block Wnt signalling activity in colorectal cancer cells.

Trabid

Trabid belongs to a small family of mammalian OTU (ovarian tumour) domain proteins that also contains A20 and Cezanne. The OTU domain has a classical cysteine protease signature, and A20 and Cezanne have been shown to exhibit de-ubiquitylating (DUB) activity. A20 is a negative regulator of NFκB signalling and inflammation, and Cezanne is also capable of downregulating NFκB-mediated transcription. The function of Trabid is disclosed herein for the first time.

Importantly, we show that Trabid loss-of-function reduces Wnt pathway activity, so according to the present invention any depletion or inhibition of Trabid (e.g. of its deubiquitylation activity) is beneficial for treatment of colorectal cancer and/or other Wnt-related disorders or diseases.

It should be noted that Wnt pathway activity is needed for the maintenance of stem cell compartments (e.g. in the intestine, and in other cells such as the hematopoietic system). Thus, agonists of the Wnt pathway (such as Trabid or activators/inducers of Trabid) may find application in stimulation of stem cell activity. Clearly, care would need to be taken in practicing this embodiment of the invention to balance the beneficial effects of overactivating the pathway against any negative oncogenic effects.

Two distinguishing features of Trabid are a conserved D>A substitution in the putative active site of its OTU domain, and multiple zinc fingers in its N-terminus that are neither found in A20 nor in Cezanne. These zinc fingers are of the NZF type, and are the ubiquitin-binding motifs. Notably, *Drosophila* contains only one member of this OTU protein family, which exhibits both of these features, and is thus an ortholog of mammalian Trabid. Furthermore, it should be noted that there are several structurally different types of ubiquitin binding domains—the zinc finger type domain has only recently been described. These domains exist in a wide range of proteins, and exist in proteins for which no ubiquitinase or deubiquitylase activity has been demonstrated.

It is noteworthy that Trabid is demonstrated to have DUB activity, because it possesses a D>A substitution in its predicted catalytic triad. This substitution is unusual, and might have been taken as an indication that Trabid would not possess deubiquitylase activity. However, we show that this substitution is compatible with DUB activity. Without wishing to be bound by theory, it may advantageously lead to a specific shape of the active site that would be sensitive selectively to inhibitors that may not affect the active sites of other OTU domains, allowing greater selectivity/specificity in inhibitors according to the present invention.

We also disclose a futher Trabid activity: E3 ubiquitin ligase activity. Evidence for this is shown in example 12 (note the less ubiquitylated beta-catenin and less ubiquitylated global protein after Trabid depletion). Thus we demonstrate for the first time that Trabid has E3 ubiquitin ligase activity, and that the inhibition of this activity is relevant for reduction of Wnt pathway activity. This Trabid activity is likely mediated by its NZF finger region, probably via the ubiquitin-binding motifs mediating or contributing to the E3 ubiquitin ligase activity. It is interesting to note that the Trabid relative A20 has both DUB activity and E3 ubiquitin ligase activity, both of which are important for its function. Thus the invention relates to the use of recombinant or purified Trabid as arm E3 ubiquitin ligase. The invention further relates to the manipulation of Wnt signalling by manipulation of Trabid E3 ubiquitin ligase activity, preferably the invention relates to reduction of Wnt signalling by reduction of Trabid E3 ubiquitin ligase activity.

The sequence of *Drosophila* Trabid (dTrabid) may be found in accession number NP_649931 (or AAF54429). The term 'Trabid' refers to the protein or to a homologue thereof. Preferably the Trabid of the invention is mammalian Trabid, preferably mouse Trabid (accession number CAD67576 (or NP_997185), most preferably human Trabid (accession number CAB64449 (or NP_060050). References to Trabid herein preferably relate to the human sequence, preferably the human amino acid sequence, unless otherwise indicated by the context. The human sequence is the most clinically relevant for therapeutic aspects of the invention such as familial adenomatous polyposis (FAP), colorectal cancer and related aspects. The same applies to nucleotide sequences for Trabid referred to herein. The publicly available Trabid nucleotide sequences can be identified using the accession numbers for the amino acid sequences provided above.

Trabid includes fragments of Trabid. Fragments may be any size, and may include deletions such as from the C-terminus or the N-terminus or one or more internal deletions or a combination of deletions. Trabid may also include mutants such as amino acid substitutions, for example the C443S mutation. Trabid may also include mutants such as addition mutants, for example an epitope tag or other marker, a histidine tag, GST tag or other such moiety for aiding purification, or other desired sequence may be added to the Trabid sequence of interest.

It is important that Trabid variants such as deletion mutants and/or substitution and/or addition mutants of combinations thereof retain the relevant biological function of interest. For example, when studying or assaying Trabid binding to ubiquitin, it is important that the zinc finger motifs are present. Equally, when studying the deubiquitylase activity of Trabid, it is important that the catalytic triad is preserved. Clearly, when the functions are studied separately, then it will be acceptable to separate the parts of the Trabid molecule which provide the separate functions. For example, the N-terminal domain of Trabid is involved in ubiquitin binding, while the C-terminal domain is involved in deubiquitylase activity. Naturally the Trabid molecule functions as a whole in its biological setting and thus preferably the whole (full length) Trabid is used in the methods and techniques described herein. It must also be noted that whilst it is important for Trabid polypeptides to retain their function in order to be regarded as Trabid fragments, there are embodiments of the invention in which the function may be deliberately ablated or compromised by mutation. One example of such a Trabid mutant is a C443S Trabid. C443 is one of the catalytic triad. Thus, the C443S mutant is a catalytically inactive Trabid useful in the present invention. Thus in one aspect the invention relates to Trabid or a fragment thereof wherein said Trabid or fragment comprises a C443 mutation, preferably the C443S mutation.

Fragments of Trabid may also find application in the present invention. Preferably fragments are at least 10 contiguous amino acids in length, preferably at least 20 contiguous amino acids in length, preferably at least 30 contiguous amino acids in length, preferably at least 50 contiguous amino acids in length, preferably at least 100 contiguous amino acids in length, preferably at least 150 contiguous amino acids in length, preferably at least 200 contiguous amino acids in length, preferably at least 250 contiguous amino acids in length, preferably at least 300 contiguous amino acids in length, preferably at least 350 contiguous amino acids in length, preferably at least 400 contiguous amino acids in length, preferably at least 450 contiguous amino acids in length, preferably at least 500 contiguous amino acids in length, preferably at least 550 contiguous amino acids in length, preferably at least 600 contiguous amino acids in length, preferably at least 650 contiguous amino acids in length, preferably at least 700 contiguous amino acids in length, preferably at least 707 contiguous amino acids in length, most preferably full length with respect to human wild type Trabid.

A preferred Trabid of the invention is Trabid fragment comprising aa355-708. This finds particular application in the assessment of Trabid deubiquitylase activity. A preferred Trabid of the invention is Trabid fragment comprising aa1-354. This finds particular application in the assessment of binding of ubiquitin.

In order to be regarded as a Trabid polypeptide, the polypeptide of interest must be a homologue of human Trabid as discussed above. In this regard, preferably the Trabid shows sequence identity to human Trabid—preferably the Trabid (or fragment thereof) displays at least 30% identity to human Trabid, preferably at least 40% identity to human Trabid, preferably at least 45% identity to human Trabid, preferably at least 50% identity to human Trabid, preferably at least 55% identity to human Trabid, preferably at least 60% identity to human Trabid, preferably at least 65% identity to human Trabid, preferably at least 70% identity to human Trabid, preferably at least 75% identity to human Trabid, preferably at least 80% identity to human Trabid, preferably at least 85% identity to human Trabid, preferably at least 90% identity to human Trabid, preferably at least 95% identity to human Trabid, preferably at least 98% identity to human Trabid, preferably at least 99% identity to human Trabid, or even more. The same applies to nucleotide sequences encoding Trabid, when variation taking account of the degeneracy of the genetic code must also be taken into account. Identity is preferably judged along the length of the Trabid (Or fragment thereof) of interest.

When studying or assaying the deubiquitylase activity of Trabid, then it is important to use a Trabid polypeptide which comprises the deubiquitylase catalytic domain of Trabid. This catalytic domain is associated with the ovarian tumour domain (OTU domain) of Trabid. The catalytic domain is preferably the C-terminus of Trabid, preferably amino acids 355-708 of mouse or human Trabid. Preferably the hTrabCT 355-708 Trabid polypeptide is used.

Preferably Trabid is recombinant or purified Trabid. Preferably Trabid is recombinant Trabid.

Trabid is preferably prepared by recombinant means. Typically the Trabid polypeptide of interest is expressed from an appropriate nucleotide sequence borne on a plasmid in *E. coli*, and the resulting polypeptide purified therefrom using standard procedures known to a person skilled in the art.

'Modulating Trabid activity' has its normal meaning in the art, i.e. to manipulate Trabid activity by raising or lowering it. This may be accomplished by manipulating the activity of Trabid itself e.g. using inhibitors, dominant negative Trabid constructs or other suitable means, or may be accomplished by manipulating Trabid levels for example by raising or lowering its expression (e.g. at the transcriptional or translational level), raising or lowering its degradation, sequestration or other means of removal or loss of Trabid. Preferably modulating means inhibiting. Preferably inhibiting Trabid activity is accomplished using an inhibitor, a dominant negative Trabid or by reducing Trabid levels. Preferably inhibition or reduction of Trabid activity is accomplished using siRNA to Trabid to reduce its expression, or using dominant negative Trabid to reduce Trabid activity such as signalling activity.

It is important to note that the invention also relates to Trabid inhibitors and to their use in countering or bringing about effects opposed to Trabid. For example, Trabid may be used to induce or sustain or elevate TCF/LEF transcription thus Trabid inhibitor may be use to eliminate, inhibit or reduce TCF/LEF transcription, Trabid may be used in the deubiquitylation of proteins thus Trabid inhibitor may be used in the inhibition of deubiquitylation or maintenance of ubiquitin on proteins; the same applies to the other applications of Trabid disclosed herein and to the opposing effects which may advantageously be brought about using Trabid inhibitor.

Trabid inhibitor means inhibitor of Trabid function. This may advantageously be a separate molecule to the Trabid molecule, for example one which binds to Trabid to bring about inhibition. Alternatively a Trabid inhibitor may be an entity which reduces Trabid levels for example an siRNA which reduces Trabid expression. Alternatively a Trabid inhibitor may be a dominant negative Trabid such as the catalytically inactive C443S Trabid disclosed herein, or inhibitory Trabid fragment(s). Dominant negative Trabid may be the Trabid N-terminal such as Trabid aa1-350, or may be the Trabid C-terminal such as Trabid 351-708, or may be a catalytically inactive Trabid mutant such as a Trabid C443 mutant, e.g. Trabid C443S, or a fragment thereof. Preferably dominant negative Trabid comprises the catalytically inactive Trabid or a fragment thereof, preferably Trabid 351-708 C443S.

Preferably Trabid inhibitor is siRNA to Trabid, or dominant negative Trabid such as Trabid C443S.

Ubiquitin

Numerous cell signalling processes are catalysed or controlled by the post translational modification of proteins by addition or removal of ubiquitin. Ubiquitin is a conserved protein of 76 amino acid residues. This fundamental ubiquitin unit may be polymerised into polyubiquitin chains. The individual ubiquitin blocks within these chains are connected by isopeptide bonds bridging a specific lysine residue of one ubiquitin and the carboxyl group of residue G76 of the next ubiquitin. There are at least two modes for this isopeptide linkage—the K48 and the K63 types. Poly ubiquitin chains built from K48 linkages tend to signal proteasome degradation of the protein to which they are attached. Chains built via K63 bonds typically signal nonproteolytic outcomes. Furthermore, the chemical structure and length of the chains can also influence signalling events. Preferably the polyubiquitin chains of the present invention are K63 chains.

In vitro ubiquitin chemistry has been well characterised in the art. For example, Pickart and Raasi (2005 Methods in Enzymology Volume 399 pages 21-36) describe controlled synthesis of polyubiquitin chains in considerable detail.

Ubiquitin groups are removed by deubiquitinylating enzymes (such as deubiquitylase, deubiquitinylating enzyme or 'DUB'). In order to study the action of deubiquitinylating enzymes, ubiquitin containing substrates which give rise to visualisable products following deubiquitylation action are used. A number of fluorescent ubiquitin derivatives useful as highly sensitive substrates for these enzymes are disclosed in Tirat et al (2005 Analytical Biochemistry Volume 343 pages 244-255).

Within the family of deubiquitinylating enzymes are several subgroups. Otubains are a recently identified family of deubiquitinlylating enzymes that belong to the ovarian tumour (OTU) superfamily of proteins. Nanao et al (2004 EMBO Volume 5 page 783-788) disclose the crystal structure of human otubain. The active site is described, and a model for otubain ubiquitin binding is proposed. An overview of the otubain family of deubiquifinylating enzymes can be found in Balakirev et al (2003 EMBO Volume 4 pages 517-522). Details of the cleavage site used by these proteases are presented (exactly at the ubiquitin-polypeptide junction) and new peptidases belonging to this family are described. Various reagents such as antiubiquitin antibodies and the like are described in these publications.

K63-linked Ubiquitin

The inventors have observed binding specificity of Trabid for K63-linked ubiquitin chains. Furthermore, this binding specificity is mediated by Trabid's Zn fingers. In other words, we disclose that Trabid has binding specificity for K63-linked ubiquitin via its zinc finger(s). The K63 selectivity is striking. This enables further uses and applications of the invention.

Thus, the invention relates to polypeptide(s) comprising one or more of the Trabid Zn fingers, or Zn finger sequences derived therefrom, as reagents for targeting moieties such as proteins to K63-linked ubiquitin chains, and to uses thereof. In particular the invention finds application in the NFκB pathway where there are robust examples of functionally relevant events of this nature.

By way of illustration of the utility/industrial application of the invention, it should be noted that that the DUB and/or Ub-binding activities, in particular the K63-linked ubiquitin binding activity, of Trabid is required for its function in SW480 colorectal cancer cells or Wnt stimulated cells (see examples and FIG. 10D; see also FIG. 19).

Thus the invention provides a polypeptide comprising
(i) at least one amino acid sequence selected from the group consisting of Trabid aa4-32, Trabid aa84-112 and Trabid aa149-177, or (ii) at least one amino acid sequence having at least 25% identity to a full length amino acid sequence of (i), wherein the structural zinc finger core residues of said amino acid sequence of (i) are retained;
wherein said polypeptide comprises at least two zinc finger domains, and wherein if said polypeptide comprises full length wild type Trabid, said polypeptide comprises at least one further amino acid in addition thereto.

In another aspect, the invention provides a polypeptide as described above wherein the at least one amino acid sequence of (ii) has at least 33% identity to a full length amino acid sequence of (i), wherein the structural zinc finger core residues of said amino acid sequence of (i) are retained and wherein the ubiquitin binding residues in the hydrophobic interface are retained.

In another aspect, the invention provides a polypeptide as described above which binds to K63-linked ubiquitin.

In another aspect, the invention provides a polypeptide comprising
(i) an amino acid sequence of interest; and
(ii) a polypeptide as described above.

In another aspect, the invention provides a polypeptide comprising
(i) an amino acid sequence of interest; and
(ii) a Trabid polypeptide that binds to K63-linked ubiquitin; wherein said Trabid polypeptide of (ii) comprises at least two zinc finger domains wherein said zinc finger domains comprise at least one zinc finger signature sequence from at least one Trabid NZF zinc finger. In another aspect, the invention provides a nucleic acid comprising a nucleotide sequence encoding a Trabid polypeptide as so defined.

In another aspect, the invention provides use of a polypeptide as described above or use of a Trabid polypeptide as described above in the targeting of a moiety of interest to K63-linked ubiquitin.

Suitably said moiety of interest is a protease.

Suitably said moiety of interest is a label.

In another aspect, the invention provides a nucleic acid comprising a nucleotide sequence encoding a polypeptide as described above.

Preferred K63-linked ubiquitin selective Trabid polypeptides comprise amino acids x to y of Trabid, preferably human Trabid, wherein x is 1 or 4 an d y is selected from 1 to 4, and y is selected from 177 to 354; suitably x is 1 or 4 and y is 177, 350 or 354.

A suitable K63-linked ubiquitin selective Trabid polypeptide that binds specifically to K63-linked ubiquitin is Trabid NT (Trabid N-terminus) 1-354.

A suitable shorter K63-linked ubiquitin selective Trabid polypeptide comprises the region spanning all 3 NZF fingers namely Trabid 4-177.

Trabid Zn fingers

The individual Zn fingers of Trabid are NZF type zinc fingers.

Each of these may bind to mono-ubiquitin with modest affinity (Kd 100-400 microM, with reference to Alam et al 2004 (Embo J. vol 23, pp 1411-1421—incorporated herein by reference)), since each conforms equally well to the signature of ubiquitin-binding NZFs determined by Alam et al 2004 (ibid), based on the structure of the Np14 NZF-ubiquitin complex. Therefore individual Trabid NZFs appear equivalent or even interchangeable for some applications.

However, it must be noted that individual NZFs may not exhibit specificity for K63-linked chains on their own (i.e. as polypeptides comprising only a single Zn finger) since NZF of Np14 binds to the commonly recognised '1441' surface of an individual ubiquitin monomer. Thus preferably a K63-selective Trabid polypeptide according to the present invention comprises at least two ZnFs such as Trabid NZFs.

A 'Trabid NZF' is an amino acid sequence corresponding to or derived from the sequence of a Trabid Zn finger. Where the amino acid sequence is 'derived from' the sequence of a Trabid Zn finger, this means it possesses a degree of amino acid sequence identity to at least one Trabid Zn finger sequence, and possesses the core signature of ubiquitin-binding NZFs determined by Alam et al 2004 (ibid). Degrees of sequence identity are as discussed above and preferably relate to sequence including the core NZF signature sequence. In these embodiments preferably sequence identity is judged across the complete sequence corresponding to the Trabid NZF(s), typically the 28 amino acid ZnF domain itself.

The locations of the three individual Zn fingers (NZFs) on Trabid are: NZF1 4-32, NZF2 84-112, NZF3 149-177.

Zn fingers may be combined on a single polypeptide. Combination of any two NZFs, (including duplication e.g. repetition of two identical fingers) may bind ubiquitin with higher affinity than a single NZF, and may show specificity.

Suitably when two fingers are used, they are fingers comprised by Trabid amino acids 4-112 or 84-177.

Combination of all 3 Trabid NZFs is likely to bind with higher affinity to ubiquitin, and show-enhanced specificity for K63 ubiquitin.

Greater numbers of ZnFs such as more than three ZnFs may provide enhanced binding and/or enhanced specificity for K63 ubiquitin. Preferably multiples of 3 NZFs are used (e.g. duplication of Trabid amino acids 4-177).

The order of occurrence of individual NZFs on a single polypeptide according to the present invention is unlikely to significantly affect binding/specificity. The skilled worker can easily optimise such order. Preferably the naturally occurring order is retained.

Spacing

Spacer sequences (i.e. sequences occurring between individual ZnFs) are unlikely to contribute directly to binding/specificity. Preferably the naturally occurring Trabid spacings and/or spacer sequences are used.

The NZF1-NZF2 spacing is 51 amino acids; the NZF2-NZF3 spacing is 36 amino acids; the NZF1-NZF3 spacing is 116 amino acids.

Precise spacing may be flexible and may be chosen by the operator. For example, spacing varies between 21-85 amino acids (NZF1-NZF2), or 26-113 amino acids (NZF2-NZF3) between different Trabid orthologs in different species. Notwithstanding this, each Trabid ortholog appears to have at least one short interval of 21-53 amino acids (typically between NZF1 and NZF2) and therefore at least one short interval of 21-53 amino acids between ZnFs is preferred. Preferably spacing amino acid sequence is 21-113 amino acids in length between individual ZnFs.

Predicted structural core residues of NZFs (based on structure of Np14; Wang et al 2003, JBC vol 278, pp 20225-20234—incorporated herein by reference) comprise:
W7, C10, C13, N17, C24, C27 (NZF1)
W88, C90, C93, N97, C104, C107 (NZF2)
W153, C155, C158, N162, C169, C172 (NZF3)

Point mutations in any of these (e.g. to alanine) may disrupt the core structure, and may reduce or eliminate ubiqiutin binding, and/or K63 specificity. Thus preferably polypeptides of the present invention retain each of these residues in the corresponding ZnF sequence(s).

Predicted ubiquitin-binding residues in the hydrophobic interface (based on Np14 NZF-ubiquitin complex; Alam et al, 2004) comprise:

(C13) T14, Y15, M26 (C27) (NZF1)
(C93) T94, Y95, Q106 (C107) (NZF2)
(C158) T159, Y160, V171 (C172) (NZF3)

The ubiquitin binding signature is 'T, Y/F, aliphatic' in the above positions flanking the zinc-coordinating C2 and C4; in hTrabid the residues in these positions (flanking the second and fourth zinc co-ordinating C) are T, Y, M (ZnF1), T, Y, Q (ZnF2) and T, Y, V (ZnF3).

Point mutations in any of these (e.g. T L, Y V) may reduce or eliminate ubiquitin binding (and/or K63 specificity), but are not likely to destroy the structure.

Thus preferably polypeptides of the present invention retain the ubiquitin binding signature in the corresponding ZnF sequence(s); preferably polypeptides of the present invention retain each of these residues in the corresponding ZnF sequence(s).

Moieties of Interest

Moieties of interest such as tags and/or target sequences may be attached to the polypeptide of the invention in any suitable manner. Suitably they may be attached by recombinant production of a polypeptide incorporating the desired elements into the polypeptide of the invention (so-called 'fusion proteins'). In this embodiment suitably attachment is to the C-terminus or N-terminus, preferably the C-terminus.

K63-selectivity or K63-specificity

An assay for K63-specificity is presented in the examples section (in particular with reference to FIG. 9A and described in methods therein).

The Kd for K63-linked ubiquitin chains is expected to be higher than affinity for mono-ubiquitin (which is expected to be ~100-400 microM for mono-ubiquitin; see above).

Preference for K63-linked versus K48-linked ubiquitin chains is estimated to be 10-100×.

Further Applications

The K63 binding reagent is useful for targeting moieties to K63 linked ubiquitin, in medical uses and/or industrial uses.

For example, the invention finds application in the enforcement of changes in cellular homeostasis of K63 ubiquitin chains. In order to influence K63-chain dependent cellular physiology K63 binding specificity may be employed to target an effector entity into the proximity of K63 ubiquitin chains. Effector entities may comprise protease domains e.g. to cleave or degrade ubiquitin chains and/or substrate protein; E3 ubiquitin ligases to degrade ubiquitin chains and/or substrate protein; or any other moiety which is desired to target to K63 ubiquitin chains.

For tagging/labelling embodiments, the invention may be applied to the detection of K63 ubiquitin chains in free form or attached to substrate proteins, for example in the study of:
   the subcellular detection of K63 ubiquitin chains (and/or substrate proteins)
   the biochemical enrichment of K63 ubiquitin chains (and/or substrate proteins)

The tag/label may be any suitable tag or label known in the art such as an epitope marker or a fluor or an enzymatic activity or an isotope or any other suitable detectable moiety including for example chemical labels (e.g. covalent attachment of label using standard chemical coupling); genetic labels (e.g. Fusion proteins or protein splice products).

More functional moieties include tags or labels such as affinity handles (for example single or multiple antibody tags; protein affinity tags such as tandem tag, streptavidin tag); fluorescent tags (e.g. FlAsH tag, standard fluorescent labels such as FITC or PE, quantum dots, GFP or other fluorescent proteins); enzymatic tags (for example HRP); tags to change cellular physiology by targeting K63 chain associated proteins (for example a protease or an E3 ubiquitin ligase with the possibility to degrade the substrate protein of the K63 ubiquitin chain).

Mutations of Trabid's K63 binding regions may be made. Such mutants include mutation of one or more of the Zn fingers, or the C155A mutant or other mutation affecting the K63-binding activity.

Wnt/APC

The terms 'Wnt pathway activity' and 'TCF transcription activity' are used interchangeably herein.

The research on which the invention is based involves a strong *Drosophila* APC mutation that interferes with both its Wnt signalling and adhesion functions. This missense mutation affects its most conserved domain (called Armadillo Repeat Domain, ARD), a putative protein interaction domain whose function in APC is poorly understood or the prior art. We have identified a conserved protein (Trabid) whose biological function was not previously known. We disclosed that this protein binds to wild-type but not mutant ARD. Trabid is a nucleo-cytoplasmic protein with de-ubiquitylating activity. Our evidence shows that Trabid contributes to the Wnt signalling activity in colorectal cancer cells.

We disclose the functions of Trabid in mammalian cells and in *Drosophila*, and investigate whether it acts as regulator or effector of APC. Trabid's role(s) in Wnt signalling and/or in cell adhesion can be examined, and their functional relevance tested in colorectal cancer cells according to the present invention. This advantageously improves understanding of the molecular functions of APC and their relevance to colorectal cancer, and provides new avenues for diagnosis, treatment and/or prevention of this common disease.

Thus the invention relates to identification of molecular targets of Trabid in the Wnt signalling pathway in various human cell lines including colorectal cancer cells, by examining the appearance of ubiquitylated candidate proteins as a result of Trabid depletion by RNA interference.

In another aspect, the invention relates to use of loss-of-function approaches to test the requirement of Trabid for Wnt target gene expression and proliferation of colorectal cancer cells, and examination of its sole in Wnt signalling during the development of various model systems including *Drosophila* and *Xenopus*.

The invention is advantageously applied to Wnt target genes, in particular those shown in FIG. 10B, C.

Assays

Assays according to the present invention are described herein, particularly in the examples and in the accompanying figures.

Variants of the assays of the invention may be easily made for example by reference to the development of a plate-based assay for the binding between β-catenin and BCL9 (see FIG. 1).

Preferably assays of the invention are assays for identification of inhibitors of Trabid.

Pharmaceutical Compositions

The present invention also provides a pharmaceutical composition comprising a therapeutically effective amount of Trabid or Trabid inhibitor(s) of the present invention and a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R.

Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be administered using a minipump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be administered by a number of routes.

Where the agent is to be administered mucosally through the gastrointestinal mucosa, it should be able to remain stable during transit though the gastrointestinal tract; for example, it should be resistant to proteolytic degradation, stable at acid pH and resistant to the detergent effects of bile:

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either atone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

For some embodiments, the Trabid or Trabid inhibitor(s) of the present invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

When using Trabid, or when the Trabid inhibitor(s) comprises a protein, then said protein may be prepared in situ in the subject being treated. In this respect, nucleotide sequences encoding said protein may be delivered by use of non-viral techniques (e.g. by use of liposomes) and/or viral techniques (e.g. by use of retroviral vectors) such that the said protein is expressed from said nucleotide sequence.

In a preferred embodiment, the pharmaceutical of the present invention is administered topically. Hence, preferably the pharmaceutical is in a form that is suitable for topical delivery.

Administration

The term "administered" includes delivery by viral or non-viral techniques. Viral delivery mechanisms include but are not limited to adenoviral vectors, adeno-associated viral (AAV) vectors, herpes viral vectors, retroviral vectors, lentiviral vectors, and baculoviral vectors. Non-viral delivery mechanisms include lipid mediated transfection, liposomes, immunoliposomes, lipofectin, cationic facial amphiphiles (CFAs) and combinations thereof.

The components of the present invention may be administered alone but will generally be administered as a pharmaceutical composition—e.g. when the components are is in admixture with a suitable pharmaceutical excipient, diluent or carrier selected with regard to the intended route of administration and standard pharmaceutical practice.

For example, the components can be administered (e.g. orally or topically) in the form of tablets, capsules, ovules, elixirs, solutions or suspensions, which may contain flavouring or colouring agents, for immediate-, delayed-, modified-, sustained-, pulsed- or controlled-release applications.

If the pharmaceutical is a tablet, then the tablet may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

The routes for administration (delivery) include, but are not limited to, one or more of: oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, vaginal, epidural, sublingual.

In a preferred aspect, the pharmaceutical composition is delivered topically.

It is to be understood that not all of the components of the pharmaceutical need be administered by the same route. Likewise, if the composition comprises more than one active component, then those components may be administered by different routes.

If a component of the present invention is administered parenterally, then examples of such administration include one or more of: intravenously, intra-arterially, intraperitoneally, intrathecally, intraventricularly, intraurethrally, intrasternally, intracranially, intramuscularly or subcutaneously administering the component; and/or by using infusion techniques.

For parenteral administration, the component is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

As indicated, the component(s) of the present invention can be administered intranasally or by inhalation and is conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1, 2-tetrafluoroethane (HFA 134A™) or 1,1,1,2,3,3,3-heptafluoropropane (HFA 277EA™), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of the agent and a suitable powder base such as lactose or starch.

Preferably the component(s) of the present invention can be administered in the form of a suppository or pessary, or it may be applied topically in the form of a gel, hydrogel, lotion, solution, cream, ointment or dusting powder. The component(s) of the present invention may also be dermally or transdermally administered, for example, by the use of a skin patch. They may also be administered by the pulmonary or rectal routes. They may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the component(s) of the present invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Pharmaceutical Combinations

The Trabid or Trabid inhibitor(s) of the present invention may be administered with one or more other pharmaceutically active substances. By way of example, the present invention covers the simultaneous, or sequential treatments with an agent according to the present invention and one or more steroids, analgesics, antivirals or other pharmaceutically active substance(s).

It will be understood that these regimes include the administration of the substances sequentially, simultaneously or together.

Dose Levels

Typically, a physician will determine the actual dosage which will be most suitable for an individual subject. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

Depending upon the need, the agent may be administered at a dose of from 0.01 to 30 mg/kg body weight, such as from 0.1 to 10 mg/kg, more preferably from 0.1 to 1 mg/kg body weight.

Formulation

The component(s) of the present invention may be formulated into a pharmaceutical composition, such as by mixing with one or more of a suitable carrier, diluent or excipient, by using techniques that are known in the art.

Treatment

It is to be appreciated that all references herein to treatment include one or more of curative, palliative and prophylactic treatment. Preferably, the term treatment includes at least curative treatment and/or prophylactic treatment. The treatment may be of one or more of those disorders mentioned herein, or related complaint.

Further Applications

The invention finds application in cancers associated with defects in the Wnt signalling pathway.

The invention may find application in hepatocellular carcinoma (HCC), Wilm's Tumour (WT), desmoids, medulloblastoma, and thyroid cancer such as anaplastic thyroid cancer.

The invention may find application in endometrian ovarian tumours, Denys-Drash syndrome, melanoma and prostate cancer.

Preferably the invention finds application in any disorder associated with enhanced TCF/LEF transcription.

Preferably the invention finds application in any disorder-associated with stabilisation and/or activation of β-catenin.

Preferably the medical indications are indications for Trabid inhibitors and/or for reduction of Trabid activity. Reduction of Trabid activity in the context of assay embodiments typically refers to biochemical activity of Trabid polypeptide reduced by other component(s) of the assay, for example a candidate inhibitor. However, reduction of Trabid activity in the context of manipulation of cells or organisms may in addition relate to reduction of Trabid levels such as reduction of Trabid expression, increase in Trabid degradation, increase in Trabid removal or sequestration or other means of reducing the activity of Trabid by reducing its presence or amount/concentration.

In the art, the only known role of ubiquitylation in the Wnt pathway was that linked to protein turnover, especially that of β-catenin. Here, we report a second and distinct role of ubiquitin in this pathway, based on our discovery that the Wnt response of mammalian cells depends on Trabid, a ubiquitin-binding and de-ubiquitylating enzyme with a preference for K634-linked ubiquitin. We used RNAi-mediated depletion to show that these activities of Trabid are required for efficient TCF-dependent transcription in Wnt-stimulated human cell lines. Furthermore, targeted deletion of Drosophila trabid revealed its role in the response to ectopic Wingless, suggesting that Trabid is a conserved positive regulator of the Wnt pathway. Finally, we also examined other signaling pathways, including NF-kappaB signaling in mammalian cells, and EGF receptor and Notch signaling in Drosophila, but found no effect of Trabid loss on these, suggesting that Trabid does not affect signaling broadly.

We show that Trabid is a bona fide DUB, capable of cleaving K63-linked ubiquitin in vitro and in vivo. This activity resides in its OTU domain, which possesses intrinsic DUB activity. Trabid orthologs exhibit a conserved amino acid substitution of an otherwise invariant aspartate so it is surprising that this variant OTU domain of Trabid orthologs is catalytically active. We disclose that the catalytic dyad comprising Cys443 and His628 in the OTU domain is critical for the DUB activity of Trabid.

Interestingly, the in vivo DUB activity of Trabid depends additionally on binding to K63-linked ubiquitin conferred by the N-terminal NZF motifs of Trabid. These motifs exhibit an unprecedented degree of preference in binding to K63-versus K48-linked ubiquitin. We show that these NZF motifs are necessary for the function of Trabid in TCF-mediated transcription, but not for its intrinsic DUB activity in vitro, so these motifs may have an auxiliary function in vivo. The NZF motifs of Trabid may serve to bind to and recruit ubiquitylated protein(s) efficiently as substrate(s) for the DUB activity of the linked OTU domain.

Trabid is a positive regulator of Wnt-mediated transcription of TCF target genes. Trabid is required for the TCF-dependent transcription, but not for the stabilization of beta-catenin, in Wnt-stimulated cells. In support of this, the TCF-mediated transcription of HCT-116 colorectal cancer cells (that harbor an activating mutation of beta-catenin) depends on Trabid. Evidently, the only clearly established ubiquitin-modified Wnt effector, beta-catenin, is not a direct target for the DUB activity of Trabid. This entirely consistent with Trabid's preference for K63- over K48-linked ubiquitin, which argues against a direct function of Trabid in proteasomal degradation.

We show that Trabid is dispensable for the transcriptional activity of LEF1 constructs that are directly fused to TADs— either the TAD from the viral protein VP16, or the C-terminus of beta-catenin, which recruits a variety of transcriptional co-factors. Thus, Trabid controls the recruitment of co-activators to the TCF-beta-catenin complex at TCF target genes during Wnt signaling.

The small but consistent reductions of the nuclear levels of beta-catenin, TCF3 and TCF4 observed in Trabid-depleted cells may reflect a role of Trabid in the nuclear retention of these proteins. However, re-expression of TCF4 and beta-catenin does not overcome the Trabid requirement of these cells.

We have shown that Trabid is also required for efficient TCF-mediated transcription in colorectal cancer cells whose Wnt pathway activity is hyperactive due to mutational inactivation of APC, or activation of beta-catenin This is entirely consistent with our epistasis analysis that places Trabid's function below activated beta-catenin. Intriguingly, we found that overexpressed Trabid accumulated in the nuclei of SW480 cells, suggesting a link between its elevated nuclear presence and its function in transcription.

Our results implicate Trabid as a molecular target for inhibitory drugs in colorectal cancer cells. Advantages include, firstly, Trabid acts on the Wnt pathway, but does not have broad effects on other signaling pathways and transcription. Secondly, the DUB activity of Trabid is critical for its function in TCF-mediated transcription, and proteases are attractive targets for specific inhibitors. Thirdly, Trabid appears to have a unique catalytic pocket, given its conserved D>A substitution in the catalytic Asp Cys His triad commonly found in cysteine proteases, so there is the potential for specific inhibitors that exhibit a preference in binding to this pocket over that of other proteases, including other OTU domains, that function in other pathways.

We found that Trabid depletion was accompanied by a reduction in the TCF3 and TCF4 levels in human embryonic kidney cells. Notably, TCF3 plays a role in maintaining skin stem cells in an undifferentiated state even in the absence of Wnt signaling, and TCF4 is required for the maintenance of stem cell compartments in the intestinal epithelium. Given the high levels of Trabid in these compartments and Trabid's role in promoting the activity of the TCF-beta-catenin complex in transcription, Trabid may have application in stem cell renewal and/or differentiation.

Figure 10:
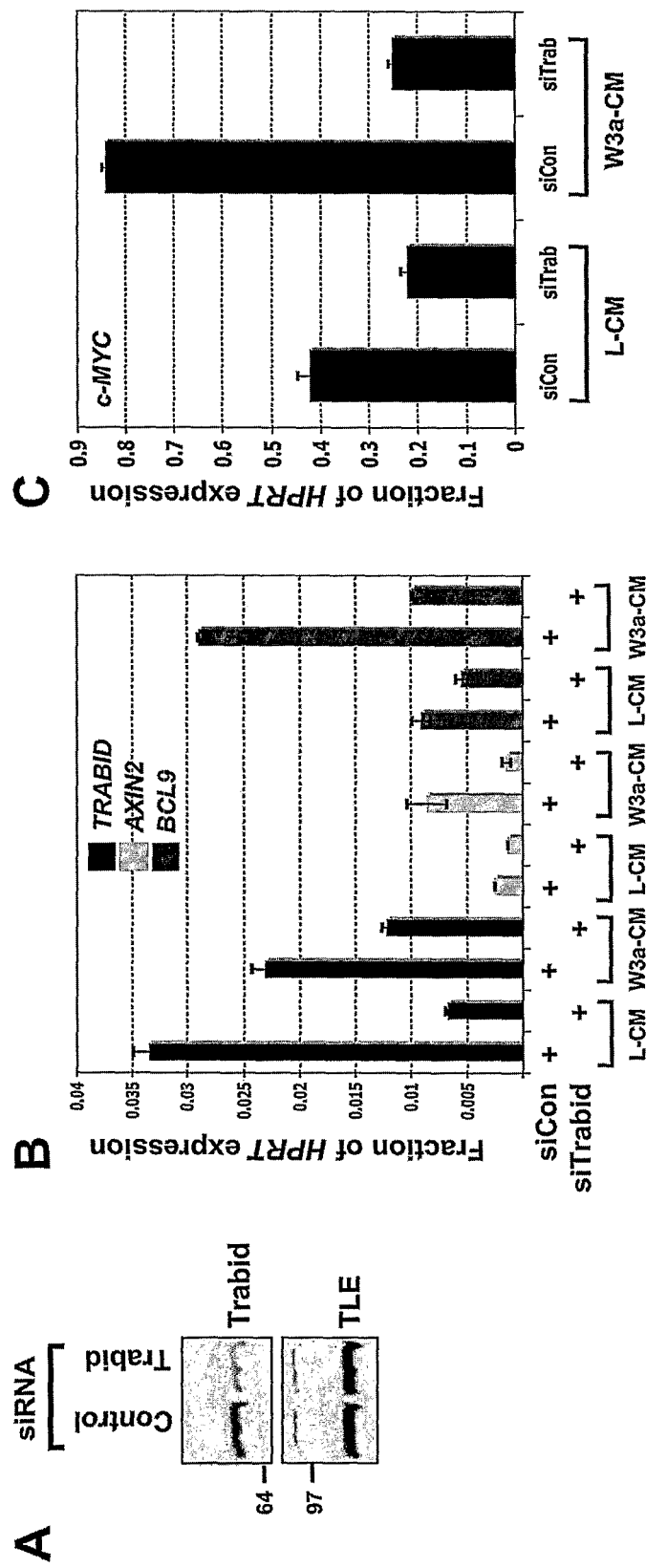
FIG. 10. RNAi-mediated depletion of Trabid causes loss of TCF-dependent transcription
(A) Western blot, showing depletion of endogenous Trabid protein in 293 cells transfected with control and Trabid-specific siRNA (internal control, α-TLE). (B, C) Real-time quantitative RT-PCR assays, after transfection of 293 cells with siRNAs as in (A), monitoring depletion of Trabid transcripts (left), and transcript levels of Wnt target genes AXIN2, BCL9 and c-MYC, as indicated, after treatment of cells with control (L-CM) or Wnt3A-conditioned medium (W3a-CM). (D) TOPFLASH luciferase assays, after transfection of SW480 cells with siRNAs, with or without re-expression of WT and mutant HA-tagged ΔsiRNA Trabid rescue constructs, as indicated; FOPFLASH values from a control luciferase reporter containing mutant TCF binding sites are also shown. Relative luciferase values are expressed as fold induction (y axis); underneath, Western blots, showing HA-Trabid expression from one representative experiment (α-tubulin, loading controls). (D) NF-κB-dependent luciferase reporter assays, in 293T cells transfected with siRNAs as in (A), and co-transfected with the expression vectors as indicated (underneath, Western blots showing expression levels). Error bars in this and subsequent figures, standard deviations from the mean, from 2-3 independent experiments (performed in duplicate).
Figure 10:
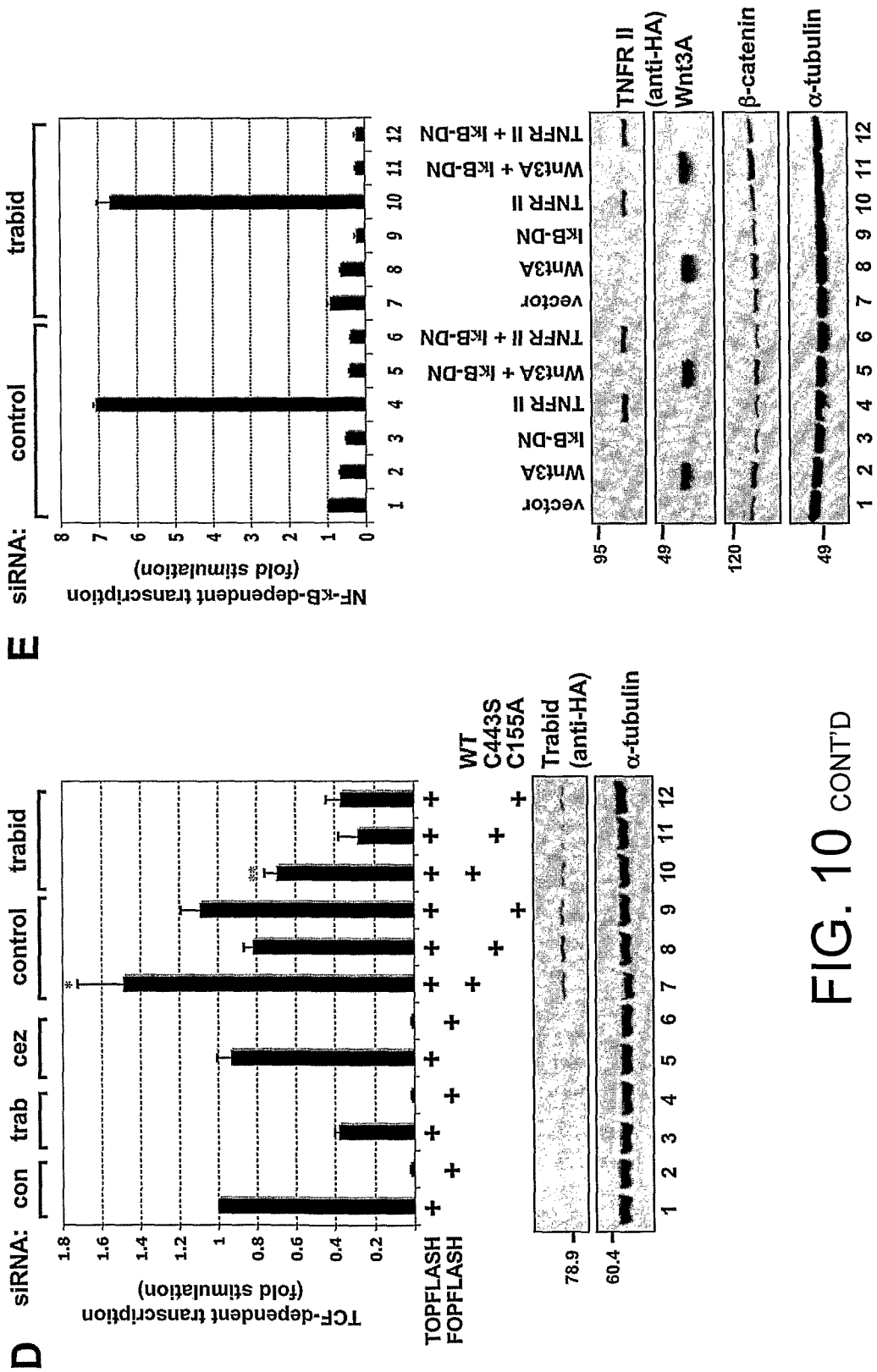

TOPFLASH assays in 293T cells, transfected with a siRNAs as in FIG. 10B, and co-transfected with (A) HA-Wnt3A, (B) dominant-negative FLAG-β-TrCP (ΔF) or (C) stabilized FLAG-β-catenin (Δ45S); underneath, Western blots from representative experiments, showing expression levels of endogenous β-catenin (A) or overexpressed protein (B, C).

Figure 12:
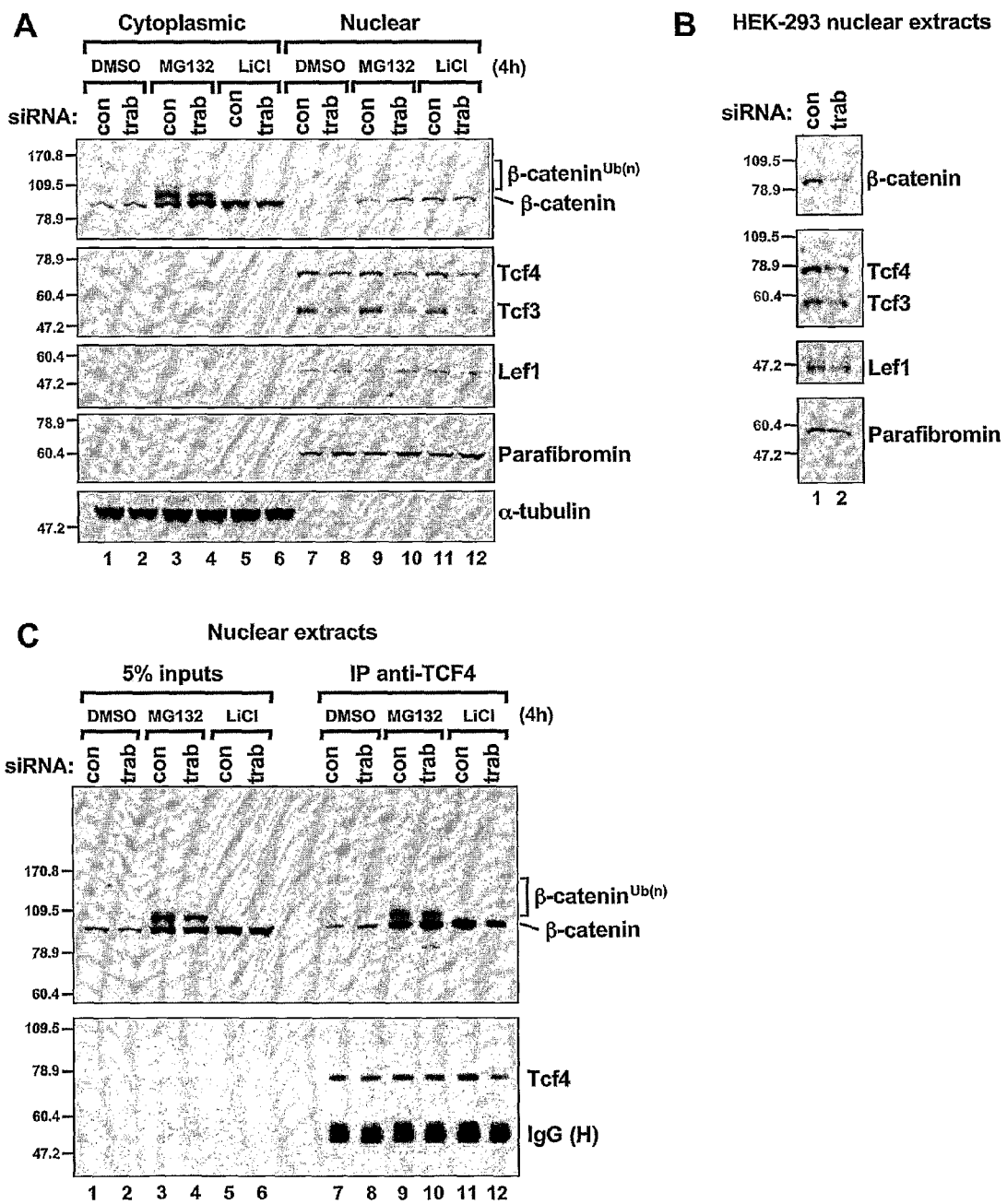

FIG. 12. Trabid depletion is accompanied by reduced TCF4 and TCF3 levels (A) Western blot of cytoplasmic and nuclear fractions of 293T cells, transfected with siRNAs as in FIG. 10B, and treated for 4 hrs with DMSO (control), 10 □MG132 or 20 mM LiCl, 24 hrs after transfection, probed sequentially with the antibodies indicated on the right. (B) Western blot (sequentially probed) of nuclear fractions of 293 cells, prepared and treated with siRNAs as in (A). (C) Co-immunoprecipitations from nuclear fractions from 293 cells (10 μg) prepared as in (A); IP, α-TCF4 antibody; Western blot, α-β-catenin antibody.

Figure 13:
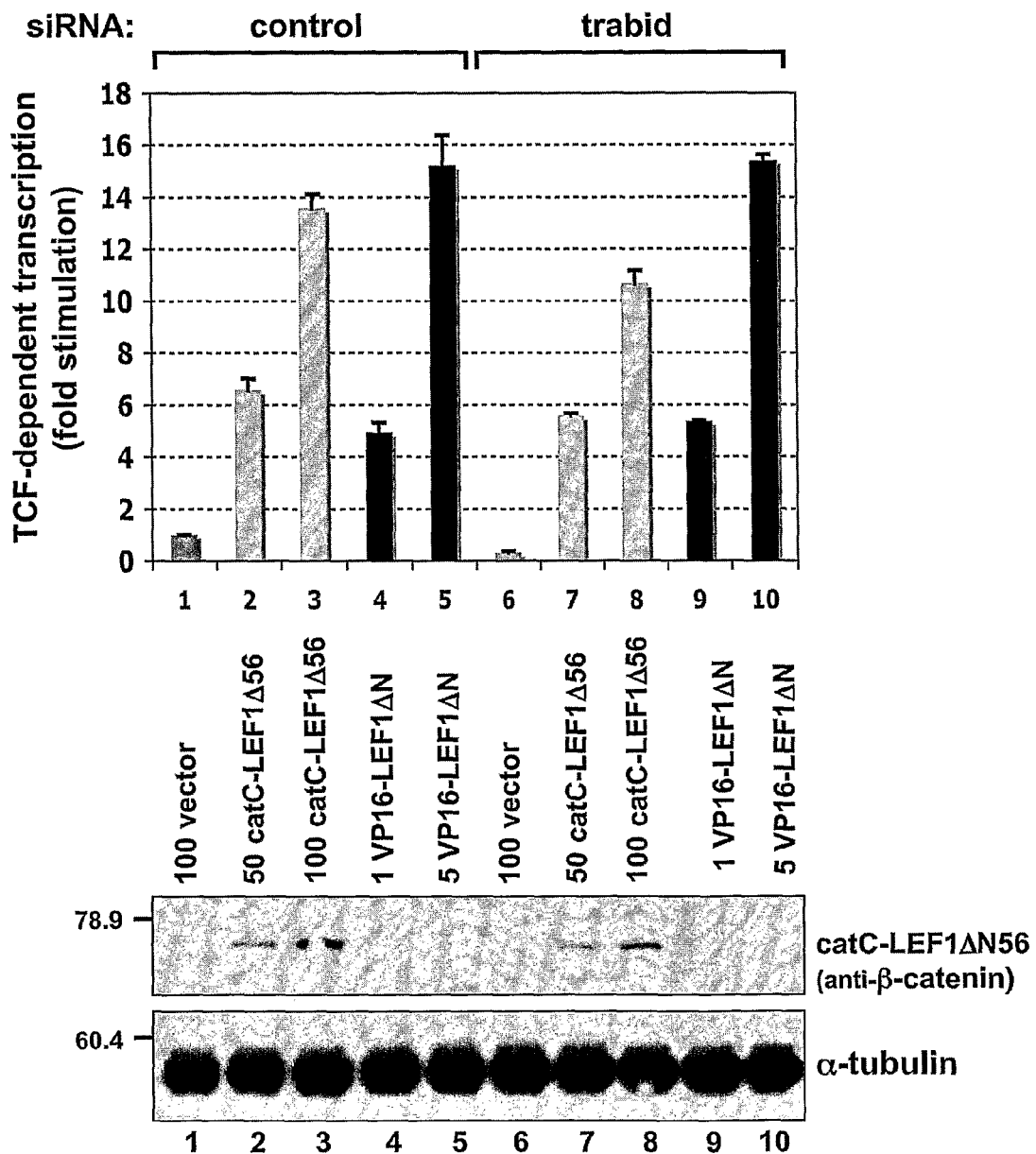

FIG. 13. Trabid is dispensable for transactivation by LEF1-TAD chimerae

TOPFLASH assays in 293T cells, transfected with siRNAs as in FIG. 10B, and co-transfected with 1-100 ng of empty vector or LEF1 chimerae, as indicated (expression levels of chimerae were calibrated, to result in comparable levels of transactivation); underneath, Western blots from a representative experiment, probed with α-β-catenin antibody showing expression levels of catC-LEF1Δ56 (note that VP16-LEF1Δ□ was undetectable at the low expression levels used to match the 10× lower activity of catC-LEF1Δ56).

Figure 14:
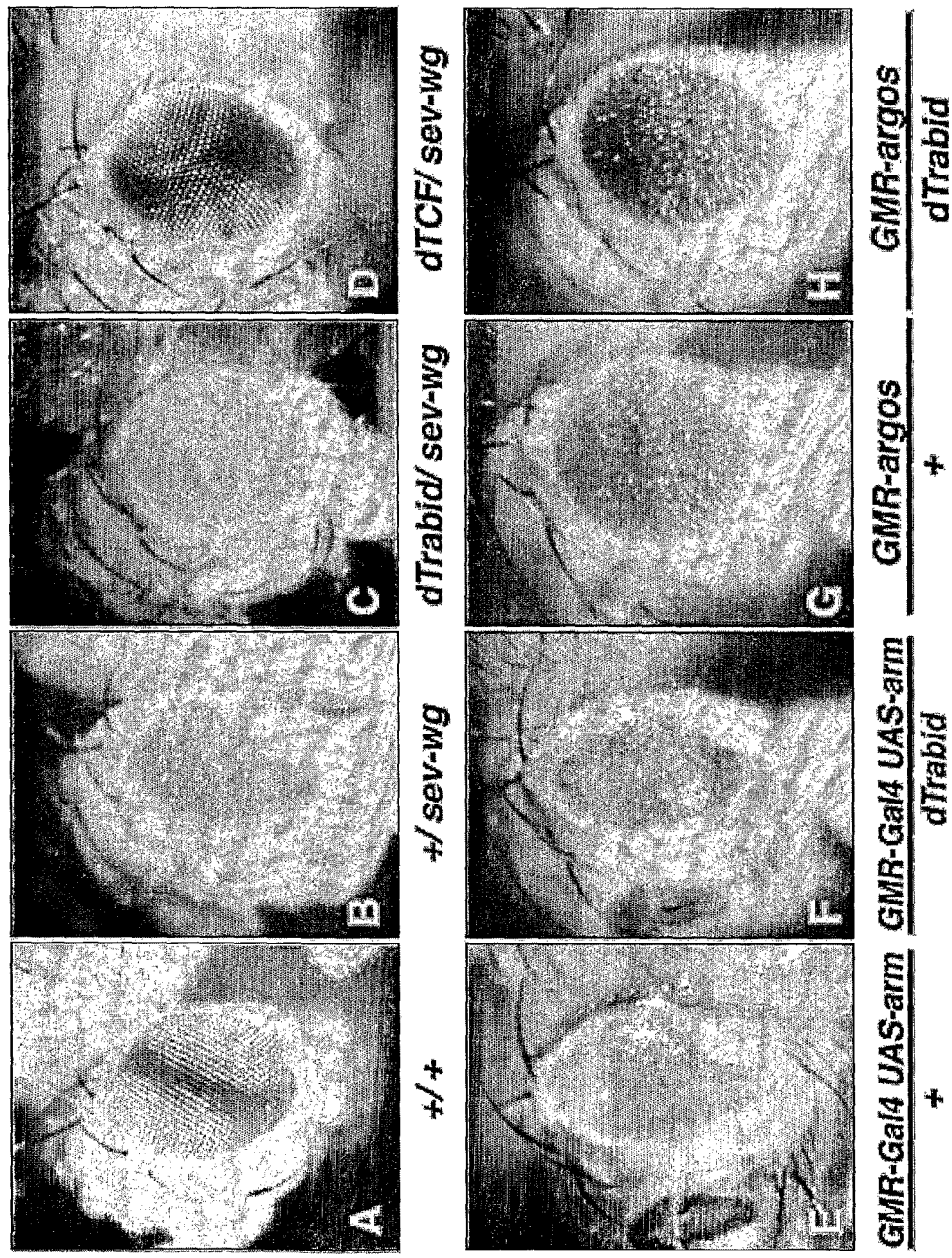

FIG. 14. dTrabid is a positive regulator of the response to ectopic Wingless signaling Eyes from y w flies, expressing (A) GAL4, or (B-D) Wingless, (E, F) Armadillo or (G, H) the Argos inhibitor of the EGF receptor; (A, B, E, G) +/+; (C, F, H) dTrabid/+; (D) dTCF³/+. dTrabid heterozygosity suppresses the rough eye phenotype due to ectopic Wingless or Armadillo (C, F), but neither that due to ectopic Argos (H) or Rhomboid.

Figure 15:
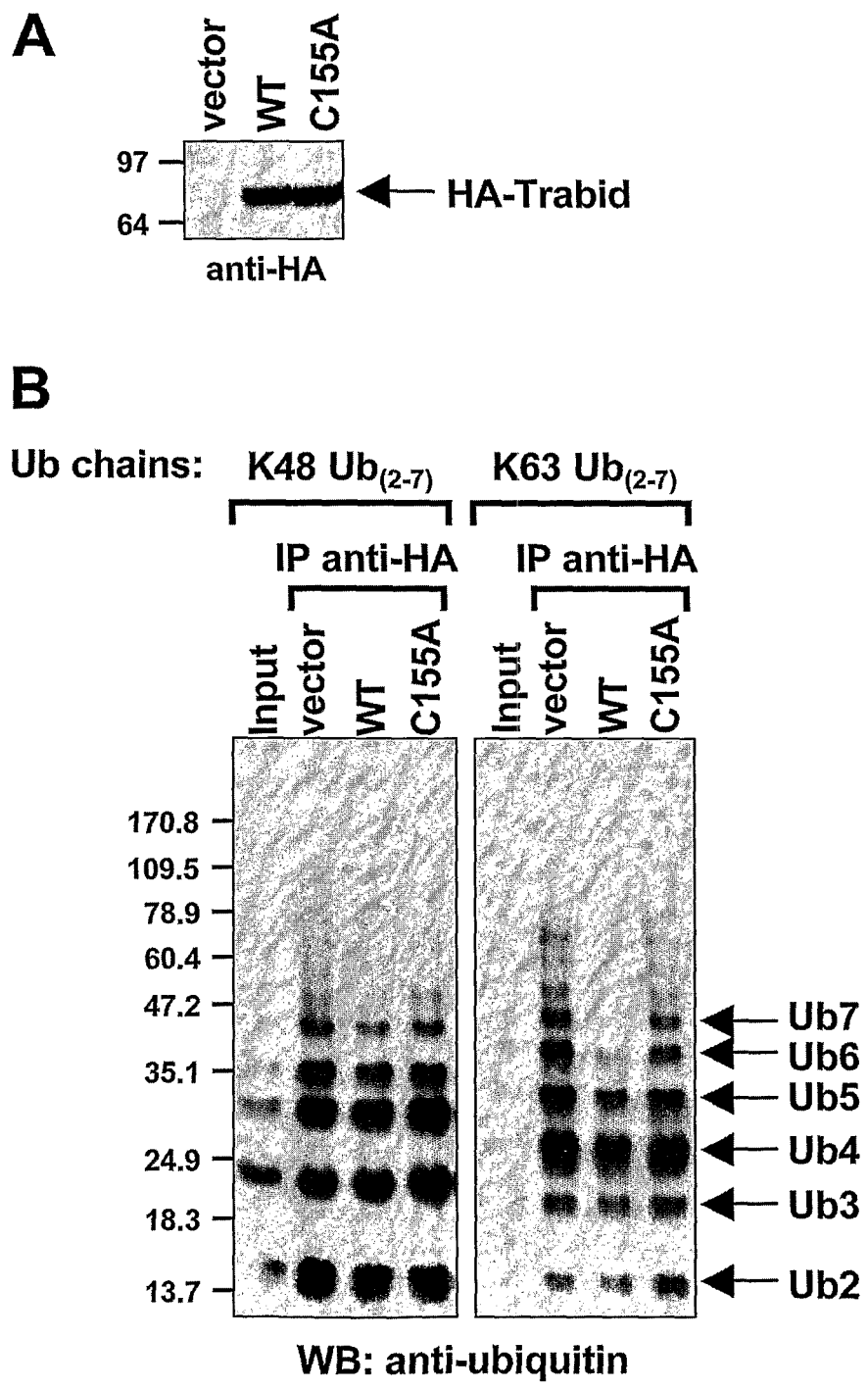

FIG. 15. The third NZF motif of Trabid is required for its DUB activity (A) Western blot from lysates of 293T cells, transfected with WT and C155A mutant HA-Trabid, after immunoprecipitation with α-HA antibody. (B) DUB assays, with immunoprecipitates from (A), incubated with K48- or K63-linked ubiquitin (UB2-7); 20 μl of the Sepharose beads were incubated with ubiquitin chains for 1 hr at 30° C.

Figure 16:
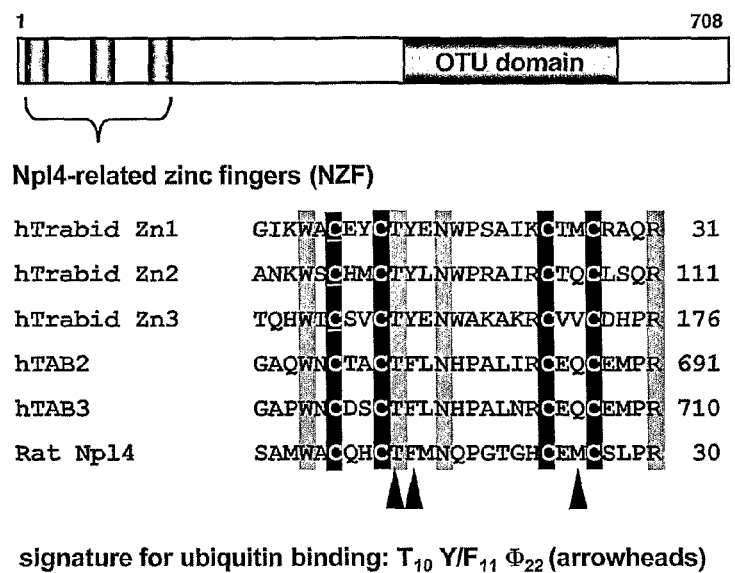

FIG. 16. Alignments of NZF motifs from different proteins

The 3 NZF motifs from human Trabid are aligned with the NZF motifs from human TAB2 and TAB3, and rat Np14 (the founder member of this motif); invariant cysteines are shaded in black, other invariant residues in grey; the first cysteines (underlined) were mutated to alanine in the 3× Zn mutant.

Figure 17:
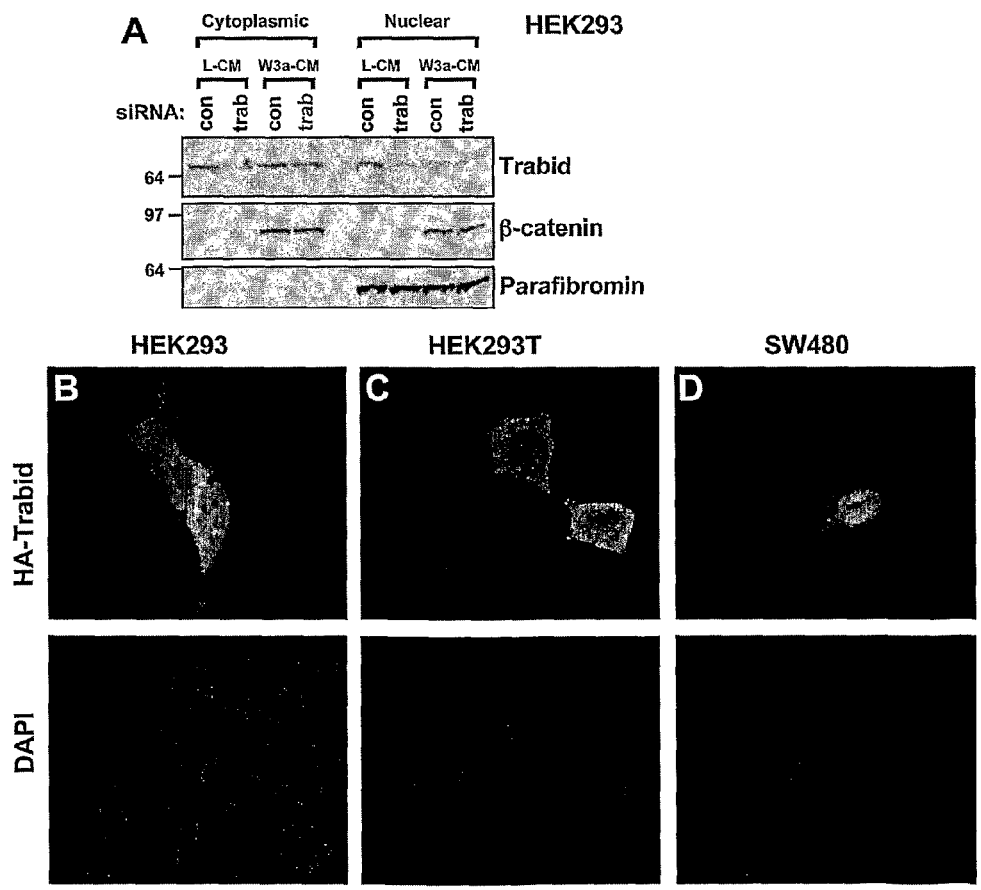

FIG. 17. Trabid is both cytoplasmic and nuclear (A) Western blot of cytoplasmic and nuclear fractions of 293 cells, transfected with siRNAs as in FIG. 10B, after treatment of cells with control (L-CM) or Wnt3A-conditioned medium (W3a-CM), probed with antibodies as indicated. (B-D) Different human cell lines as indicated, transfected with HA-Trabid, fixed and staining with α-HA antibody and DAPI (to label the nuclei). Cells were washed with PBS (+) and fixed in 1 ml pre-warmed 4% paraformaldehyde in PBS (−) for 20 min at room temperature. Subsequently, cells were permeabilized with 0.5% TritonX-100 in PBS (−) for 10 min, blocked with 5% normal goat serum for 20 min, followed by incubation for 2 h with α-HA (diluted in PBS (+) containing 1% goat serum). Cells were washed twice with PBS (+) (10 min per wash) and subsequently incubated with Alexa$^{488}$ α-rat secondary goat antibody (Molecular Probes) for 40 min and washed 3 times with PBS (+). Coverslips were mounted on glass slides using Vectashield with DAPI (Vector Laboratories). Fluorescence was visualized with an MRC 1024 confocal microscope, and images were scanned at ×600 magnification. Note the nuclear accumulation of HA-Trabid; in SW480 cells.

Figure 18:
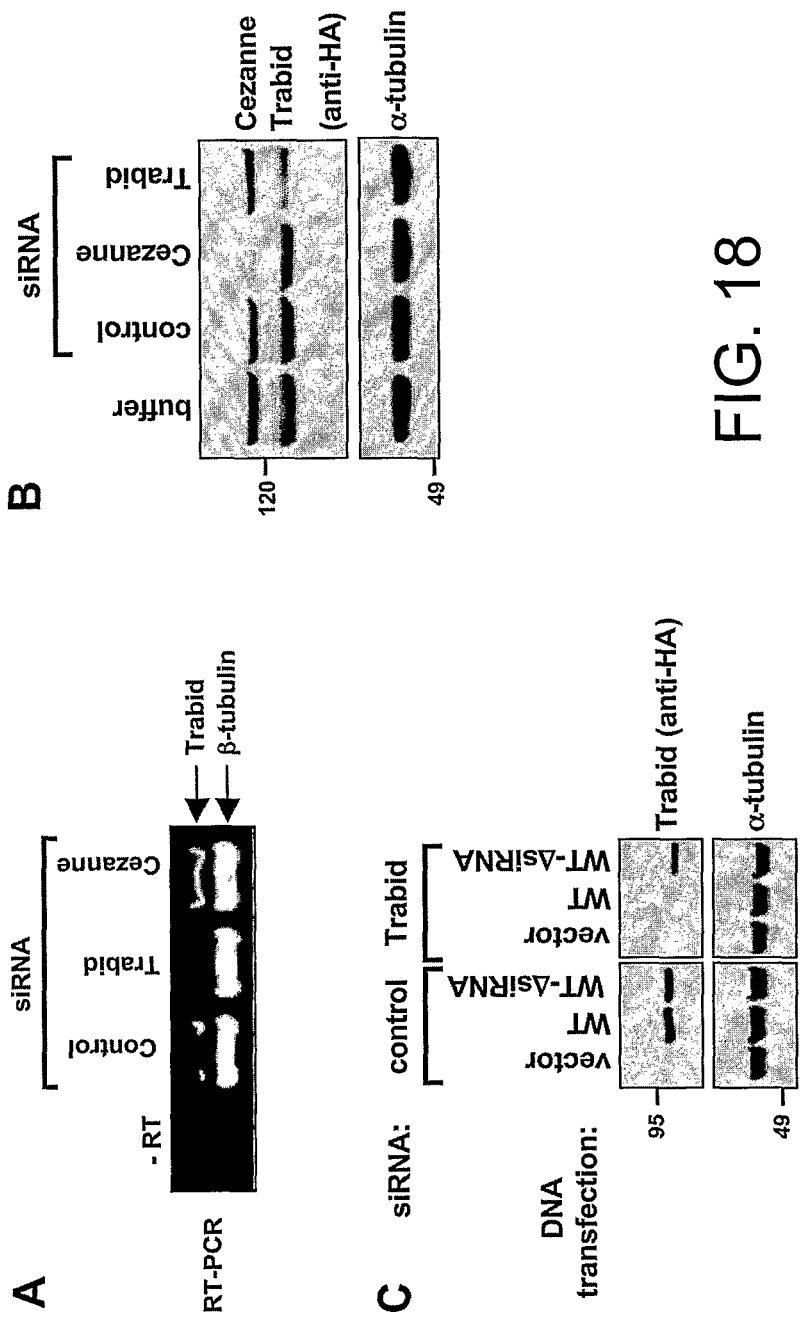

FIG. 18. Specificity of the RNAi-mediated depletion of Trabid (A) Semi-quantitative RT-PCR analysis, showing the levels of endogenous Trabid transcripts in 293T cells transfected with siRNAs as in FIG. 10D. (B) Western blots of lysates from 293T cells transfected with siRNAs as in FIG. 10D, and co-transfected with HA-tagged Cezanne and Trabid, probed with α-HA antibody. (C) Western blots of lysates from 293T cells transfected with siRNAs as in FIG. 10A, and co-transfected with HA-tagged Trabid with silent mutations (ΔsiRNA) that renders it refractory to depletion with Trabid siRNAs.

Figure 19:
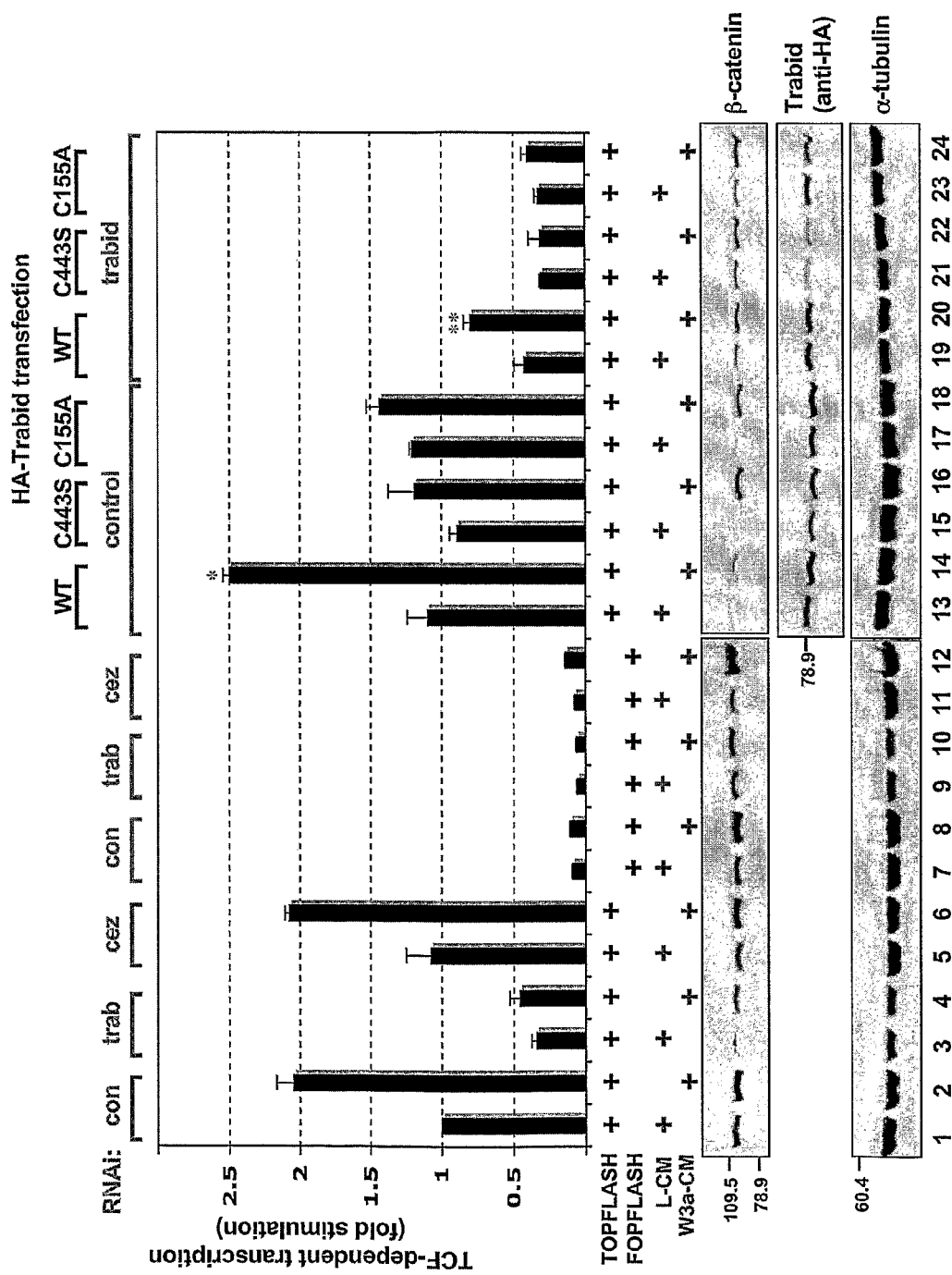

FIG. 19. RNAi-mediated depletion of Trabid causes loss of TCF-dependent transcription in Wnt3A-stimulated 293T cells TOPFLASH assays, after co-transfection of 293T cells with siRNAs and WT and mutant ΔsiRNA Trabid rescue constructs as in FIG. 10D, as indicated, with or without Wnt3A stimulation as in FIG. 10B; underneath, Western blots, showing levels of endogenous β-catenin, and HA-tagged Trabid-rescue constructs.

Figure 20:
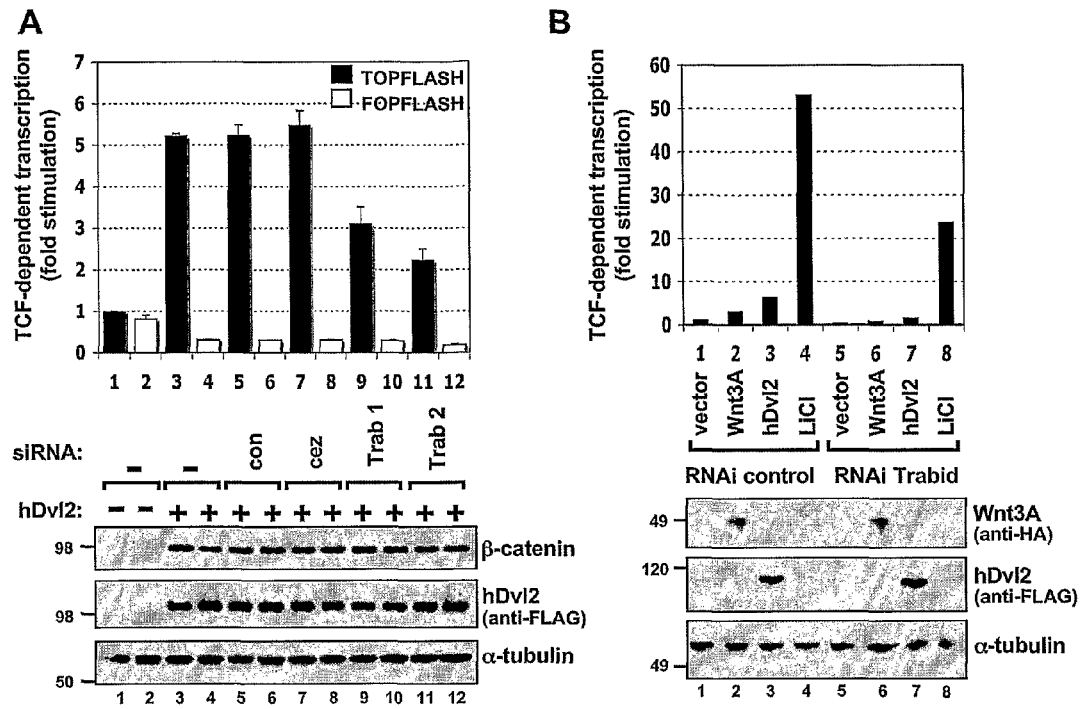

FIG. 20. Trabid acts below Dishevelled and GSK3β

(A) TOPFLASH assays of 293T cells, transfected with two different siRNAs against Trabid, or siRNA against Cezanne as in FIG. 10D, and co-transfected with empty vector or FLAG-Dv12. (B) TOPFLASH assays in 293T cells, transfected with a siRNAs as in FIG. 10B, and co-transfected with empty vector, FLAG-Dv12 or HA-Wnt3A, or treated with 10 mM LiCl for 4 hrs (lanes 4 and 8).

Figure 21:
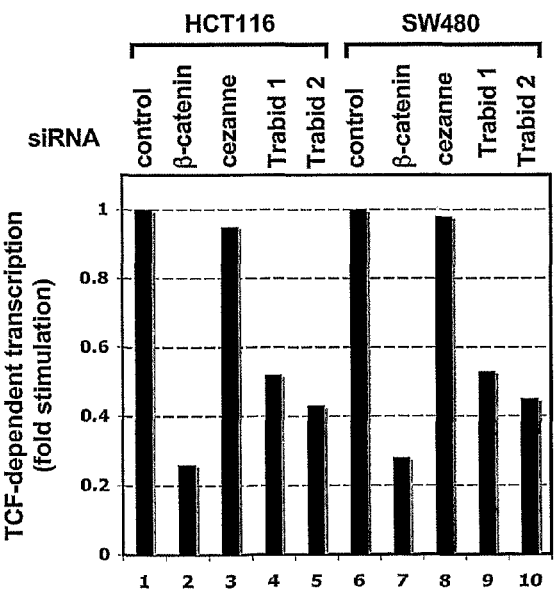

FIG. 21. Trabid is required for TCF-mediated transcription in colorectal cancer cells TOPFLASH assays of SW480 or HCT-116 colorectal cancer cells, after transfection with control siRNA, or siRNA against Trabid (two different siRNAs) or Cezanne, and against β-catenin, as a comparison.

EXAMPLES

Example 1

Identification of Proteins that Mediate the Functions of the ARD of APC in Wnt Signalling and Cell Adhesion The ARD of E-APC is critical for its association with adherens junctions, and for its function in Wnt signalling, in particular for its ability to form a complex with Axin in vivo (note however that the Axin-binding motifs of APC proteins are outside the ARD). Indeed, these functions are abrogated by a single mis-sense mutation, N175>K (corresponding to N507 in APC), which is expected to affect the binding of ARD to its ligands, based on structural considerations.

To identify proteins that mediate the functions of the ARD of APC in Wnt signalling and cell adhesion, we conducted a yeast two-hybrid screen of a mouse embryonic library with the wild-type ARD domain of APC as bait, and counter-screened the isolates with the N507>K mutant domain. This led to the identification of a protein called Trabid.

The specificities in the binding of Trabid to wild-type versus mutant ARD were subsequently confirmed in vivo by co-immunoprecipitation.

Example 2

The Function of Trabid in Wnt Signalling

We demonstrate that Trabid is a deubiquitylase enzyme ('DUB' enzyme). We further show that Trabid promotes Wnt signalling in mammalian cells.

Loss-of-function analysis, based on depletion by RNAi, revealed that Trabid (but not Cezanne) is required for efficient TCF-mediated transcription in colorectal cancer cells mutant for APC or β-actenin.

Epistasis analysis based on the same approach placed Trabid below activated β-catenin. Importantly, Trabid depletion does not, affect NFκB-mediated transcription, so its effect on TCF-mediated transcription appears to be specific.

The OTU domain of Trabid has DUB activity in vivo and in vitro, and its NZF region binds to ubiquitin chains, with a preference for K63-linked chains. Taken together, this evidence suggests that a de-ubiquitylation step is critical for efficient TCF-mediated transcription. Ubiquitin turnover at TCF target genes may be necessary for their sustained transcription during Wnt signalling. Furthermore, we also identify Trabid as a target for inhibitory drugs, and provide methods for accomplishing this (see examples below)

Example 3

Biochemical and Biological Characterisation

Trabid has been biochemically characterized according to the present invention. This has confirmed elements of its function noted above and allowed further development of assays and applications of the invention.

Figure 3:
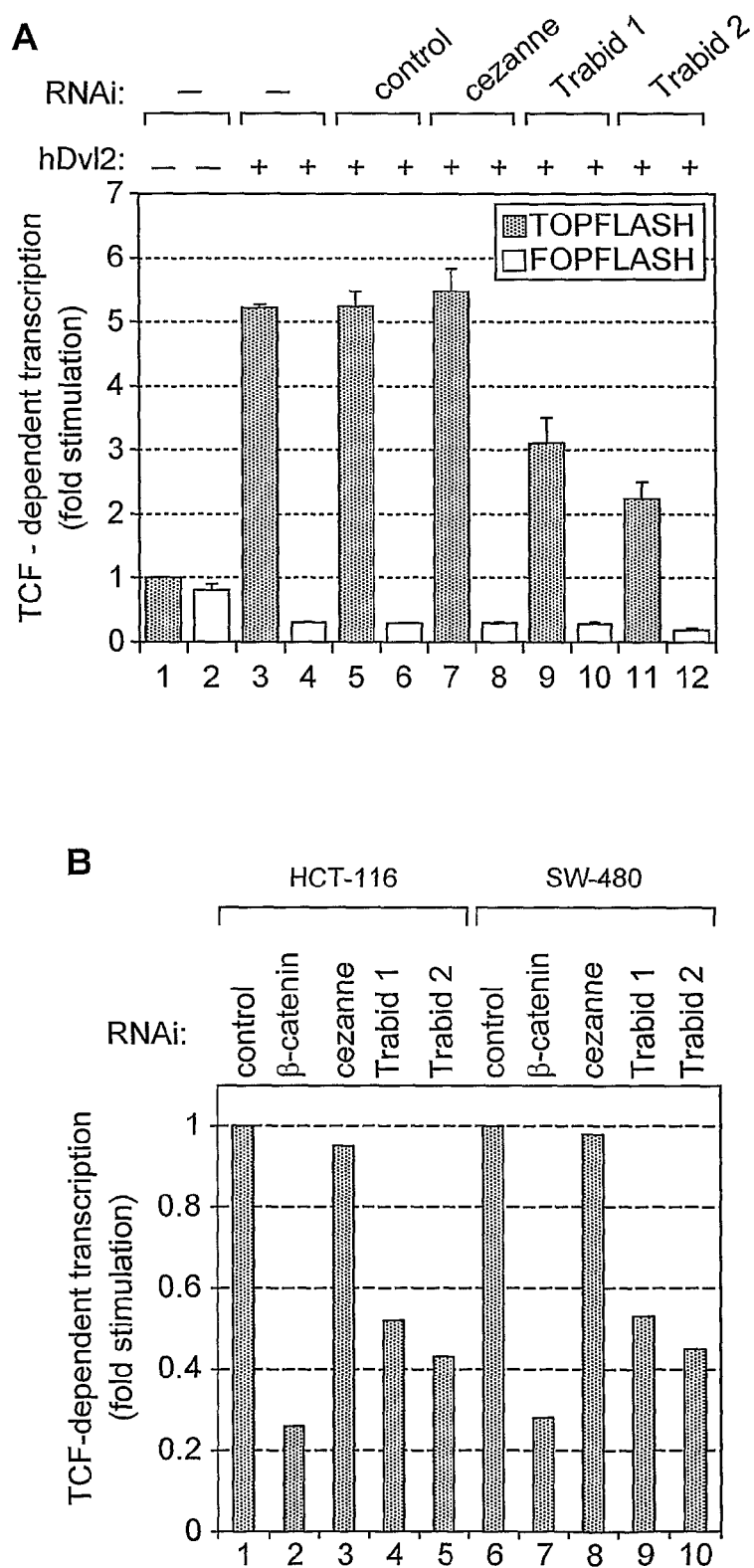
FIG. 3 shows three bar charts and two photographs.
Figure 3:
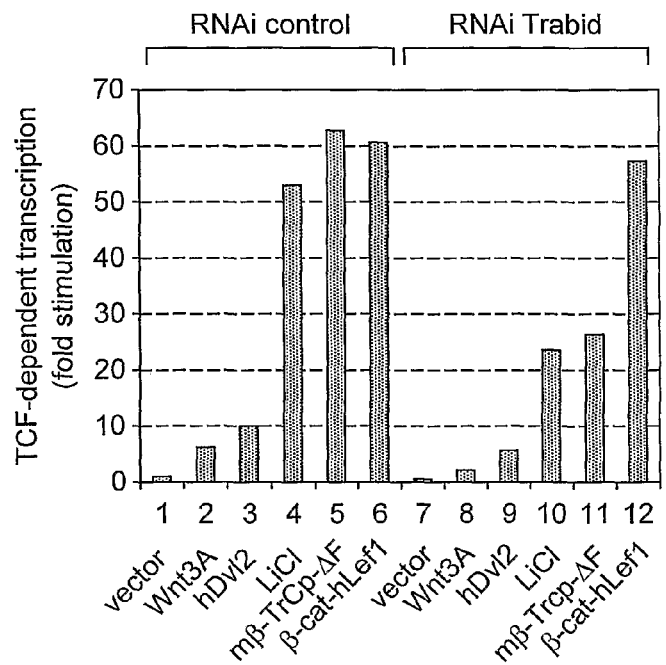
Figure 3:
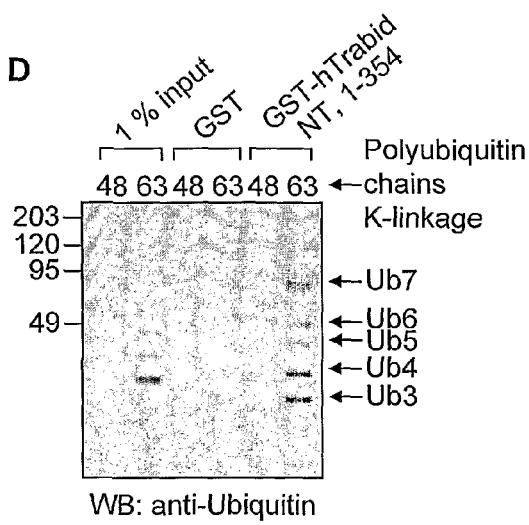
Figure 3:
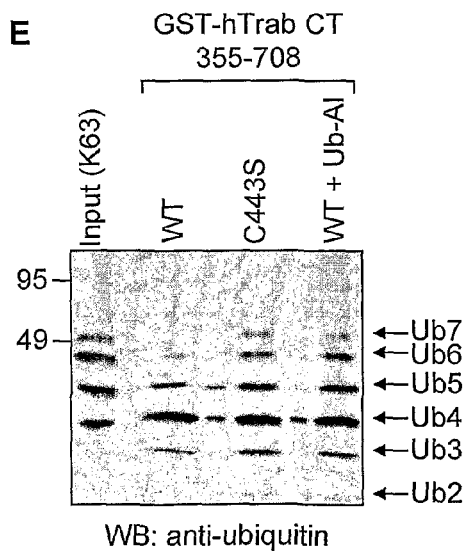

FIG. 3 shows a range of biochemical results establishing Trabid function. In particular, FIG. 3(a) and (b) show transcriptional effects mediated by Trabid. Furthermore, it is shown that inhibition of Trabid diminishes TCF mediated transcription.

Specifically, depletion of Trabid is mediated by different Trabid inhibitors. In this example the two Trabid inhibitors used are siRNAs to Trabid. The two siRNA sequences are: AGA GGT GTC TCA ACA AGC A (no 1) and AGA GGC TTC TTC AAT AAT A (no 2).

These inhibitors each reduce Dvl-stimulated TCF transcription in 293T cells (FIG. 3a), and in the colorectal cancer cell lines HCT-116 and SW-480 (FIG. 3b).

Epistasis experiments in 293T cells reveal a function for Trabid in transcriptional regulation.

We demonstrate that the N-terminus of Trabid containing three NZF fingers binds preferentially to K63 ubiquitin chains in a GST-pull-down assay FIG. 3d).

Furthermore, we experimentally demonstrate Trabid deubiquitylase activity, and further demonstrate that this activity is associated with the C-terminus of Trabid. Thus, the C-terminus harbours the OTU de-ubiquitylation domain; this Trabid activity cleaves preferentially K63 ubiquitin chains in vitro (see FIG. 3e).

Thus it is shown that Trabid is a de-ubiquitylase affecting Wnt signalling in human cells, and does so in cell lines derived from a key disease indication of the invention, i.e. colorectal cancer.

Example 4

Molecular Target(s) of Trabid in Wnt Signalling

Further evidence of functional connection between Trabid and Wnt signalling and colorectal cancer is generated.

The invention allows us to identify the protein(s) that are the physiologically relevant substrates of Trabid during Wnt signalling. Our current evidence indicates that these are nuclear proteins—such as activated β-catenin (note however that activated β-catenin is phosphorylated and thus no longer a substrate for ubiquitylation), Pygopus or Lgs/BCL9, or any of the other co-activators that are recruited by β-catenin. Trabid may also affect the transcriptional activity of β-catenin less directly, for example by inhibiting RanBP3, which has recently been shown to promote the nuclear export of βcatenin.

We use antibodies against these proteins (Sierra, J., Yoshida, T., Joazeiro, C. A. & Jones, K. A. *Genes Dev* 20, 586-600 (2006); Hendriksen, J. et al. *J Cell Biol* 171, 785-97 (2005)) and Western blotting to check the appearance of Trabid-dependent ubiquitylated forms after RNAi-mediated depletion of Trabid in established human colorectal cancer cell lines (e.g. in SW480 and HCT116 cells), or in Wnt-stimulated 293T cells.

Ubiquitylation is confirmed by simultaneous blotting with antibody against ubiquitin (or against overexpressed tagged ubiquitin). These experiments are advantageously carried out after treatment of cells with proteasome inhibitors (e.g. MG132), to maximise the chances of detecting short-lived ubiquitylated species that are expected to appear after depletion of Trabid.

These experiments provide insights into the nature of the DUB step during TCF-mediated transcription, and may reveal further detail of the mechanism by which it impacts on Wnt signalling.

Example 5

Functional Analysis of Trabid

In this example we extend our work on Trabid loss-of-function by examining the expression of endogenous Wnt target genes that are upregulated (e.g. c-myc, CD44) or down-regulated (e.g. Hath1) in SW480 and HCT116 colorectal cancer cells (mutant for ARC or β-catenin, respectively), or in Wnt-stimulated-293T cells, after RNAi-mediated depletion of Trabid (see earlier example).

In particular, we examine their rate of proliferation under these conditions. To obtain reliable results from these experiments, it may be beneficial to generate stable lines with inducible hair-pin constructs (van de Wetering, M. et al. *EMBO Rep* 4, 609-15 (2003)).

We have generated a deletion of *Drosophila* Trabid by homologous recombination. This is useful to examine whether this protein affects TCF-mediated transcription during *Drosophila* development. The analysis of this Trabid mutant is done as described for Pygopus and Legless/BCL9, nuclear Wnt signalling components whose function is required for the transcriptional activity of Armadillo/β-catenin during development and in colorectal cancer cells (see Thompson B, Townsley F M, Rosin-Arbesfeld R, Musisi H & Bienz M. *Nat Cell Biol* 4, 367-373 (2002); Kramps, T. et al. *Cell* 109, 47-60. (2002)).

We examine whether depletion of *Xenopus* Trabid by morpholino technology causes Wnt-like phenotypes, and whether this affects any of the TCF-mediated transcription events during embryonic development (Liu, F., van den Broek, O., Destree, O. & Hoppler, S. *Development* 132, 5375-85 (2005)).

Without wishing to be bound by theory, these experiments may indicate a role of Trabid in Wnt signalling during development. This can be further elucidated by generating a conditional knock-out of mouse Trabid in the intestinal epithelium (Sansom, O. J. et al. *Genes Dev* 18, 1385-90 (2004)), to examine its function in this tissue during normal development and in intestinal tumours. Trabid loss in this tissue might be expected to result in a depletion of the crypt stem cell compartment similar to loss of Tcf-4, and might suppress the incidence and size of intestinal tumours in Min mutant mice, similar to other genes that promote intestinal tumorigenesis.

Example 6

Trabid Assay

The conditions of the deubiquitylase assay described in FIG. 3 are as follows:

Trabid and Trabid variants are provided at 1.0 μg each.

They are incubated with 1.0 μg of a mixture of oligo-ubiquitin chains (Affiniti) in 20 μl buffer (150 mM KCl, 50 mM Hepes, pH 7.4, 10 mM DTT, 5% glycerol, 0.01% Triton X-100) for 60 min at 30° C.

Reactions are terminated with 2×SDS sample buffer (20% glycerol, 125 mM TrisHCL, pH 6.8, 4% SDS, 0.01 mg/ml bromophenol blue, 10 mM DTT).

Samples are resolved by SDS-PAGE, and visualised.

Results are shown in FIG. 3.

Thus Trabid activity is assayed according to the present invention.

Example 7

High Throughput Screen for Inhibitors of Trabid

In this example, methods for identifying inhibitors of Trabid are demonstrated. We disclose for the first time the biological activity of Trabid as a deubiquitylase. In this example, methods of identifying inhibitors of the deubiquitylase activity of Trabid are demonstrated.

First we characterised the de-ubiquitylating activity of recombinant Trabid in vitro (see above examples). We now demonstrate a microplate-based assay which is useful in screening for inhibitors, such as small molecule inhibitors, of this activity.

In the above examples, the function of Trabid in TCF-mediated transcription was investigated. Here we develop a high-throughput microplate assay for the deubiquitylase ('DUB') activity of Trabid.

First the DUB activity of recombinant Trabid in vitro should be taken into account. For example, its activity may advantageously be optimised, its substrate preference surveyed, and/or conditions for the assay chosen according to operator needs.

Optionally the NZF domain may be included in the Trabid used for the assay, for example in order to enhance its activity.

Figure 1:
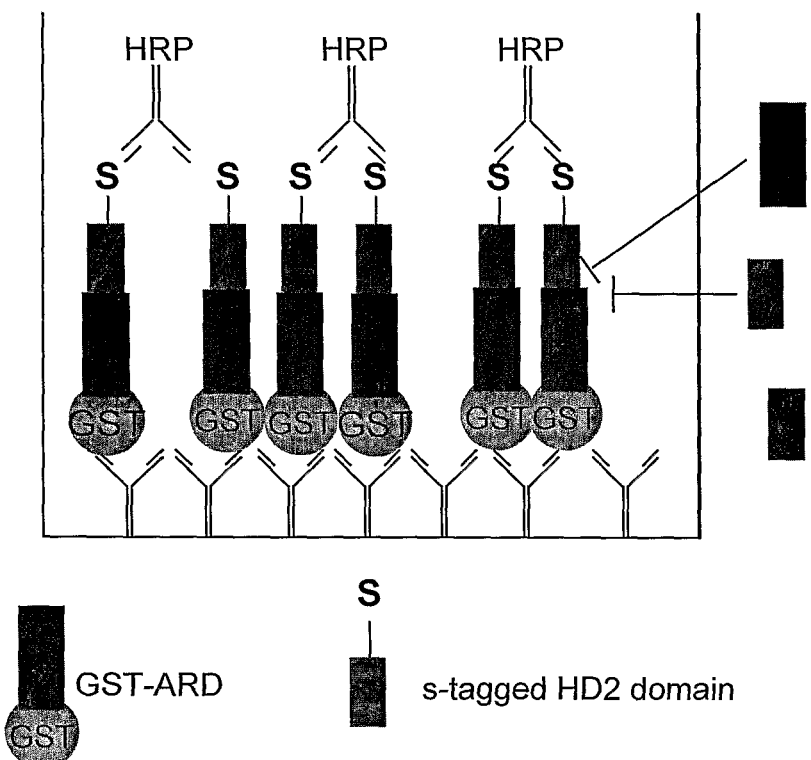
FIG. 1 shows diagrammatic illustration of a microplate assay.
Figure 2:
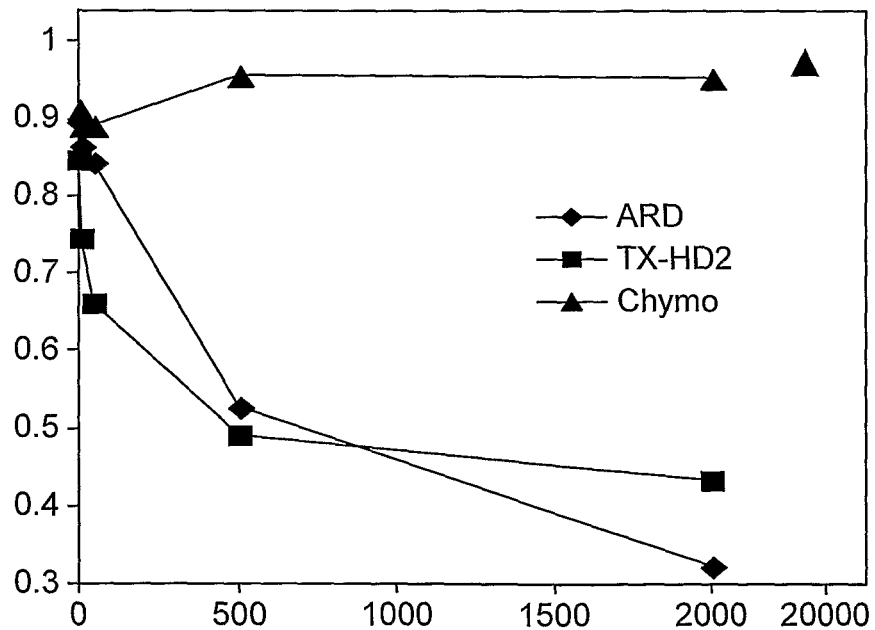
FIG. 2 shows competitive inhibition curves.

An overview of the basis for an assay of the invention is provided in FIG. 1. FIG. 1 shows the outline design of a microplate assay which is adapted for assaying the DUB activity of Trabid as described below. Thus in FIG. 1, a schematic illustration of a microplate assay described here is provided. The component proteins are ARD (blue), HD2 (red) and chymotrypsin (green), these are also labeled in the key below the diagram. ARD and HD2 are both able to inhibit the birding between GST-ARD immobilized on the plate via antibody interaction and S-tagged HD2, whereas chymotrypsin is unable to do so (represented by the individual blocks shown on the right hand side of the diagram outside the reaction vessel (microtitre well); the upper two show the symbol for inhibition (—|). The GST ARD domain construct is produced recombinantly in *E. coli*, and then attached to the inside of the microtitre wells by binding to an anti-GST antibody, which has been previously coated onto the inner surface of said wells. FIG. 2 shows competitive inhibition curves demonstrating a saturable inhibition of the interaction between GST-ARD and HD2 using either untagged ARD or Tx-tagged HD2. Chymotrypsin is unable to inhibit this interaction, even at a concentration of 20 microM.

Turning to the method for assaying Trabid, in overview this is conducted as follows: a doubly-tagged ubiquitin substrate (e.g. GST-ub-ub-S) is synthesised, immobilised, and release of the S-tag after cleavage by added bacterially expressed Trabid is monitored. Individual wells of the microtitre plate provide capacity for individual assay conditions, for example different candidate inhibitors of Trabid activity. Release of the S-tag in a particular condition indicates presence of active Trabid. Lack of release, or release at a lower level relative to the appropriate uninhibited Trabid control, indicates inhibition of Trabid activity.

Although the format of the assay may be advantageously varied according to operator needs, this example describes a preferred assay based on a bacterially expressed GST-Trabid-OTU domain construct (Trabid amino acids 355-708) that cleaves K63 ubiquitin chains in vitro, an activity that can be abolished by a mutation in the putative catalytic triad (C443A) of the OTU domain (Nanao, M. H. et al. *EMBO Rep* 5, 783-8 (2004)).

In a first step, a double-tagged poly-ubiquitin substrate is generated using the methods and reagents known in the art (Pickart, C. M. & Raasi, S. *Methods Enzymol* 399, 21-36 (2005)). This substrate is immobilised on microtitre plates by one of the tags, preferably the N-terminal GST tag. The assay is advantageously simplified by using a double-tagged poly-ubiquitin substrate. This substrate can be directly attached to the microtitre well by one tag, advantageously avoiding the need for an (anti-GST)-to-(GST-substrate)-to-(detectable tag) or other such arrangement for immobilisation. The second tag is advantageously used in detection of release following Trabid cleavage (if any).

Next, candidate inhibitor(s) and/or vehicle(s) and/or known inhibitor(s) are applied to the appropriate test and control wells respectively.

If necessary, the buffer is adjusted to permit Trabid activity (should any be possible). Preferably the buffer is as per example 6.

Next, Trabid is added.

Next, the plates are incubated to allow any Trabid action to take place. Preferably the plates are incubated as in example 6.

Optionally the reactions are then stopped by inactivation of Trabid and/or addition of a known inhibitor to all wells. Alternatively, reactions may be stopped using SDS sample buffer as in example 6.

Next, the plates are read out.

Readout of the assay is via detection of release of the tag (preferably C-terminal tag) into the supernatant after cleavage by Trabid, by comparison with reduced release (or even lack of release) when Trabid is inhibited (or inactive/absent in control wells).

In alternative embodiments, fluorescent ubiquitin derivatives could be used as substrates, such as those known in the art (e.g. see Tirat, A. et al. *Anal Biochem* 343, 244-55 (2005)). In these embodiments, readout of the assay would be via monitoring of release (or lack of release) of the fluor following ubiquitinase action (or lack of said action).

The inactive C443A Trabid mutant serves as a useful negative control in this assay. In particular, to calibrate the assay the level of release of the detectable moiety in the presence of the catalytically inactive C443A Trabid mutant may be taken as the baseline. The revel of release in the presence of the catalytically active Trabid preparation (without any inhibitor or candidate inhibitor) may be taken as the positive control. The test samples in the presence of candidate inhibitors may then be compared with the positive and negative (baseline) controls in order to aid interpretation of the results and identification of inhibitors of Trabid function.

This assay advantageously enables screening of libraries of small molecules for inhibitors of the DUB activity of Trabid. Trabid is a promising biochemical target for small molecule inhibitors, given the known structure of the OTU domain (Nanao, M. H. et al. *EMBO Rep* 5, 783-8 (2004)) and the existence of specific inhibitors of this domain (Balakirev M Y, Tcherniuk S O, Jaquinod M & Chroboczek J. *EMBO Rep* 4, 517-22 (2003)—preferably compounds to be screened are based on inhibitors described therein).

Furthermore, since the conserved D>A substitution in the catalytic triad (Makarova, K. S., Aravind, L. & Koonin, E. V. *Trends Biochem Sci* 25, 50-2 (2000)) is likely to impact on the precise architecture of Trabid's active site, the invention advantageously enables inhibitors that recognise specifically the unique shape of the OTU domain of Trabid protein(s) to be identified.

Inhibitors identified by these screen(s) may advantageously be further tested and validated in vitro and in vivo in the assays described above.

Thus, this example describes further biochemical characterisation of Trabid and small molecule inhibitors of its DUB activity. Moreover, assays for inhibitors of Trabid activity are demonstrated.

Example 8

Trabid is a Deubiquitylating Enzyme Involved in Wnt Signalling

Overview:

Negative control of Wnt signalling in mammalian cells is maintained by the constitutive targeting of β-catenin for phosphorylation (by a protein complex which includes APC, Axin and GSK-3β) and ubiquitylation (by the E3 ubiquitin ligase (β-TrCP). Ubiquitylated β-catenin is ultimately degraded by the proteasome. Wnt pathway activation results in Dishevelled-induced inactivation of the β-catenin phosphorylation complex. Non-phosphorylated β-catenin is refractory to degradation, and thus rapidly accumulates and translocates to the nucleus. Nuclear β-catenin binds to and co-activates TCF/Lef transcription factors to drive the expression of Wnt target genes.

Results

In a yeast two hybrid screen with the negative Wnt signalling component APC as bait, we have identified a mouse protein with previously unknown biological function, called Trabid. Trabid belongs to the OTU (ovarian tumour) family of deubiquitylating enzymes, which includes A20 and Cezanne. We show that Trabid possesses deubiquitylating activity, and that it also preferentially binds to K63-linked ubiquitin chains in vitro. Depletion of Trabid from HEK-293T cells by RNAi resulted in significant loss of the response of these cells to various positive Wnt components. Importantly, Trabid depletion did not affect transcription from control promoters such as CMV or NF-κB. Epistasis experiments suggest a function for Trabid in nuclear Wnt signalling. We found reduced levels of TCF transcription factors in Trabid-depleted cells, demonstrating use of Trabid in reducing responsiveness of mammalian cells, such as 293T cells, to Wnt signalling.

Example 9

Trabid is a Deubiquitylating Enzyme

Figure 4:
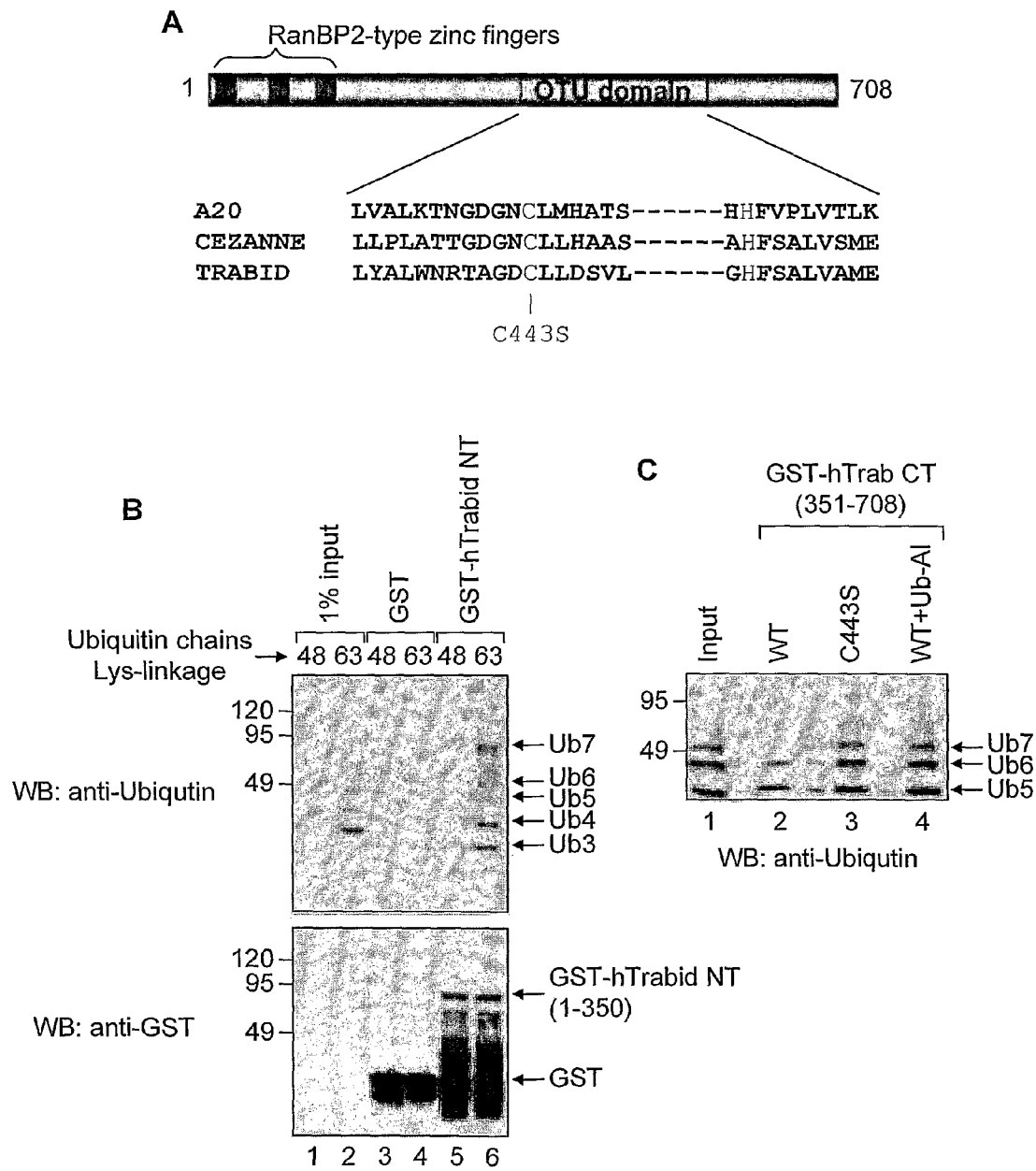
FIG. 4 shows a diagram, sequences and photographs.

FIG. 4 shows evidence demonstrating the deubiquitylase activity of Trabid.

FIG. 4(A) shows the domain composition of hTrabid and alignment of the conserved CYS and HIS boxes of three OTU family members.

A proteolytically inactive Trabid mutant (FIG. 4C, lane 3) was generated by substituting the catalytic Cys443 with Serine.

FIG. 4(B shows that the N-terminus of Trabid containing three NZFs (RanBP2-type zinc fingers) binds preferentially to K63 ubiquitin chains in a GST-pull-down assay (lane 6).

FIG. 4(C) shows that the C-terminus of Trabid harboring the OTU deubiquitylation domain cleaves preferentially K63 ubiquitin chains in vitro. Key: Ub-A1, ubiquitin aldehyde: deubiquitylase inhibitor.

Example 10

Trabid is a Positive Component of Wnt Signalling

Figure 5:
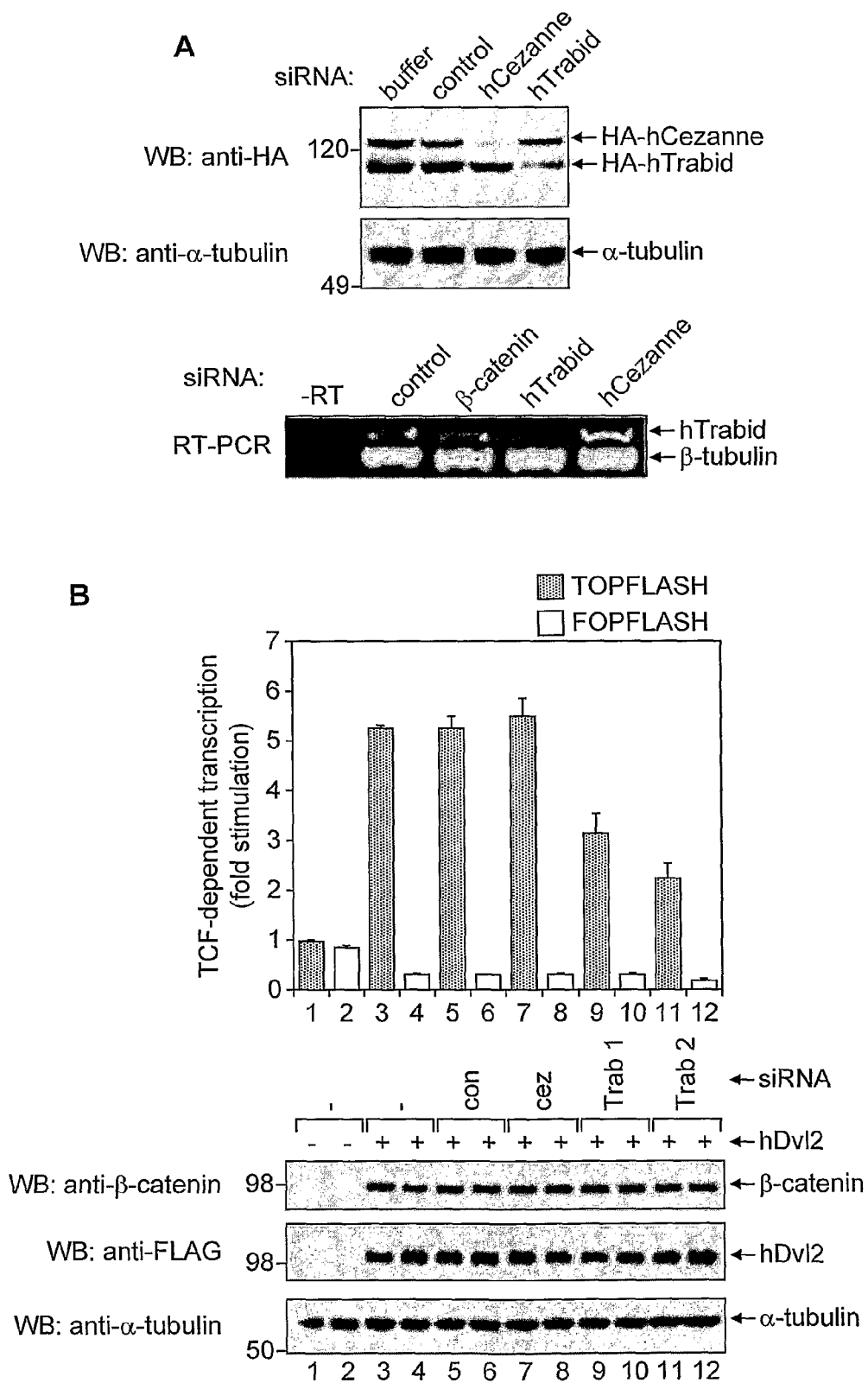
FIG. 5 shows photographs.

FIG. 5 shows the results of RNAi experiments in 293T cells which demonstrate that Trabid is a positive component of Wnt signalling.

FIG. 5(A) shows the specificity and efficiency of siRNAs. These were determined by Western blotting of ectopically-expressed, HA-tagged Trabid and Cezanne, and by RT-PCR to assess the levels of depletion of endogenous Trabid mRNA.

FIG. 5(B) shows that depletion of Trabid mediated by two different siRNAs (Trab1 and Trab2) significantly reduces Dv1-stimulated TCF transcription (TOPFLASH). FOPFLASH=negative control.

Example 11

Trabid Function in Transcriptional Regulation

Figure 6:
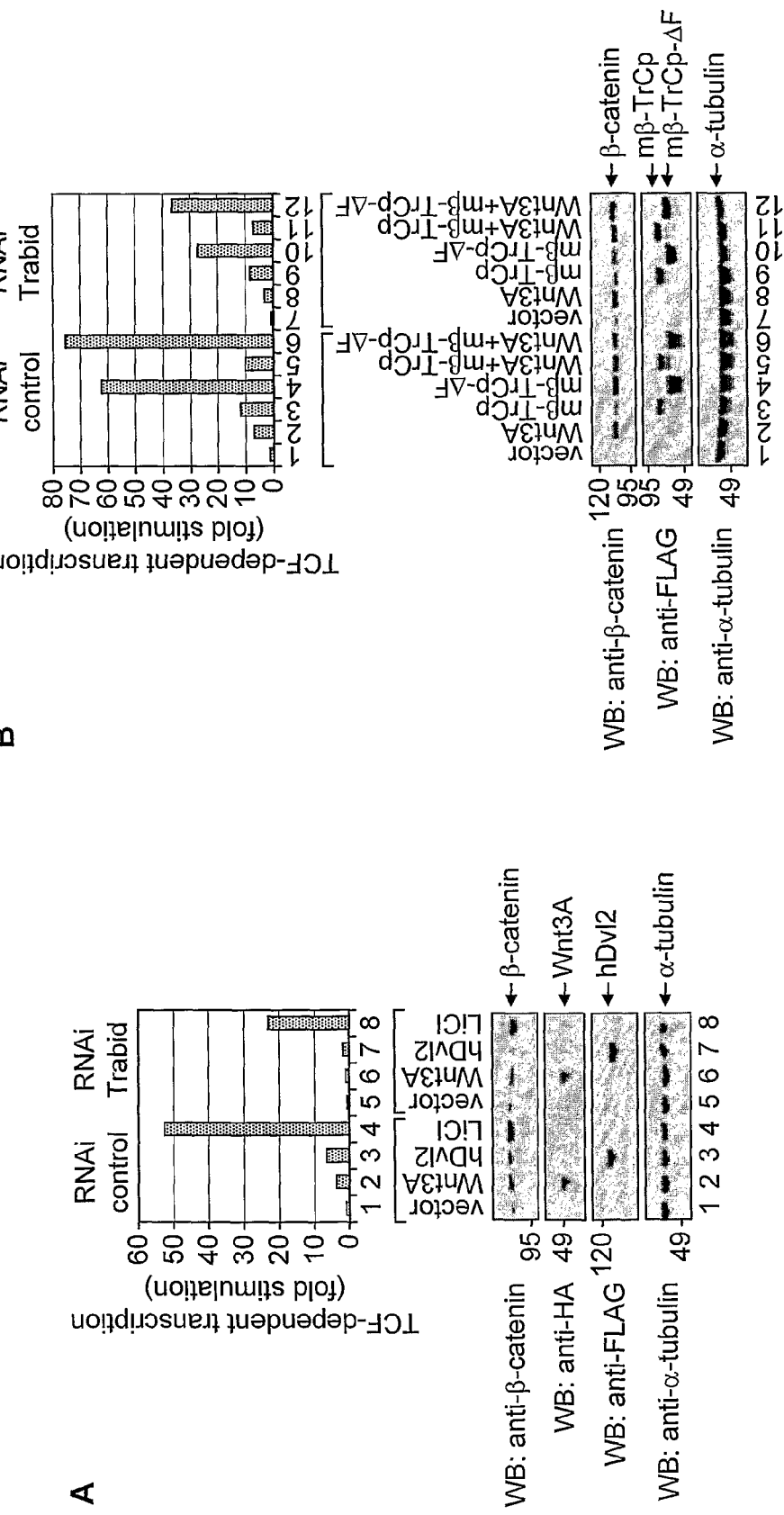
FIG. 6 shows bar charts and photographs.
Figure 6:
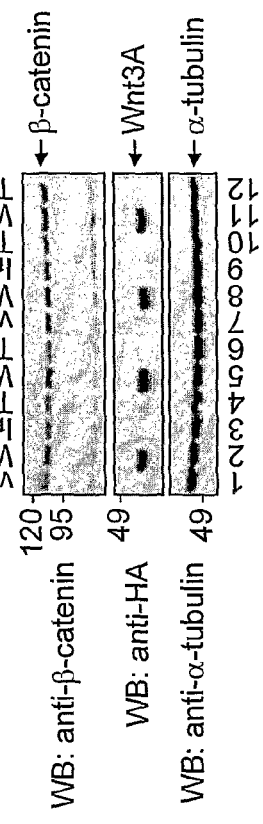
Figure 6:
Figure 6:
Figure 6:
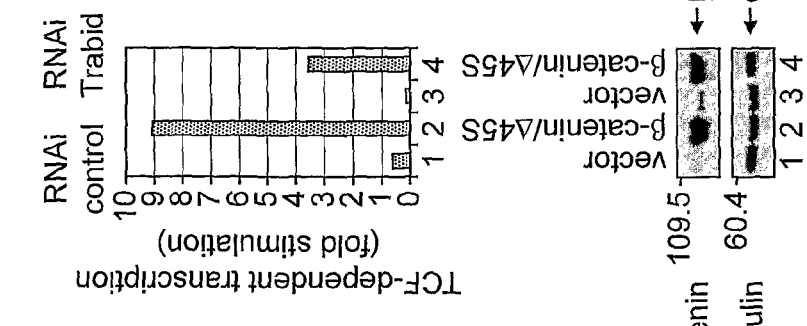

FIG. 6 shows epistasis experiments in 293T cells which demonstrate a function for Trabid in transcriptional regulation.

FIG. 6(A) shows that Wnt-3A, Dv12 and LiCl stimulation of TCF transcription were all attenuated in Trabid-depleted cells, as were activation of TCF transcription by a dominant negative β-TrCP (ΔF) (FIG. 6B) or a stabilised β-catenin mutant (Δ45S) (FIG. 6C).

FIG. 4(D) shows that in contrast, depletion of Trabid had no effect on TNFR-induced stimulation of NF-κB transcription. The same is true for CMV promoter driven transcription.

This evidence demonstrates a specific role for Trabid in Wnt signalling.

Example 12

Effect of Trabid Depletion on Wnt Pathway

Figure 7:
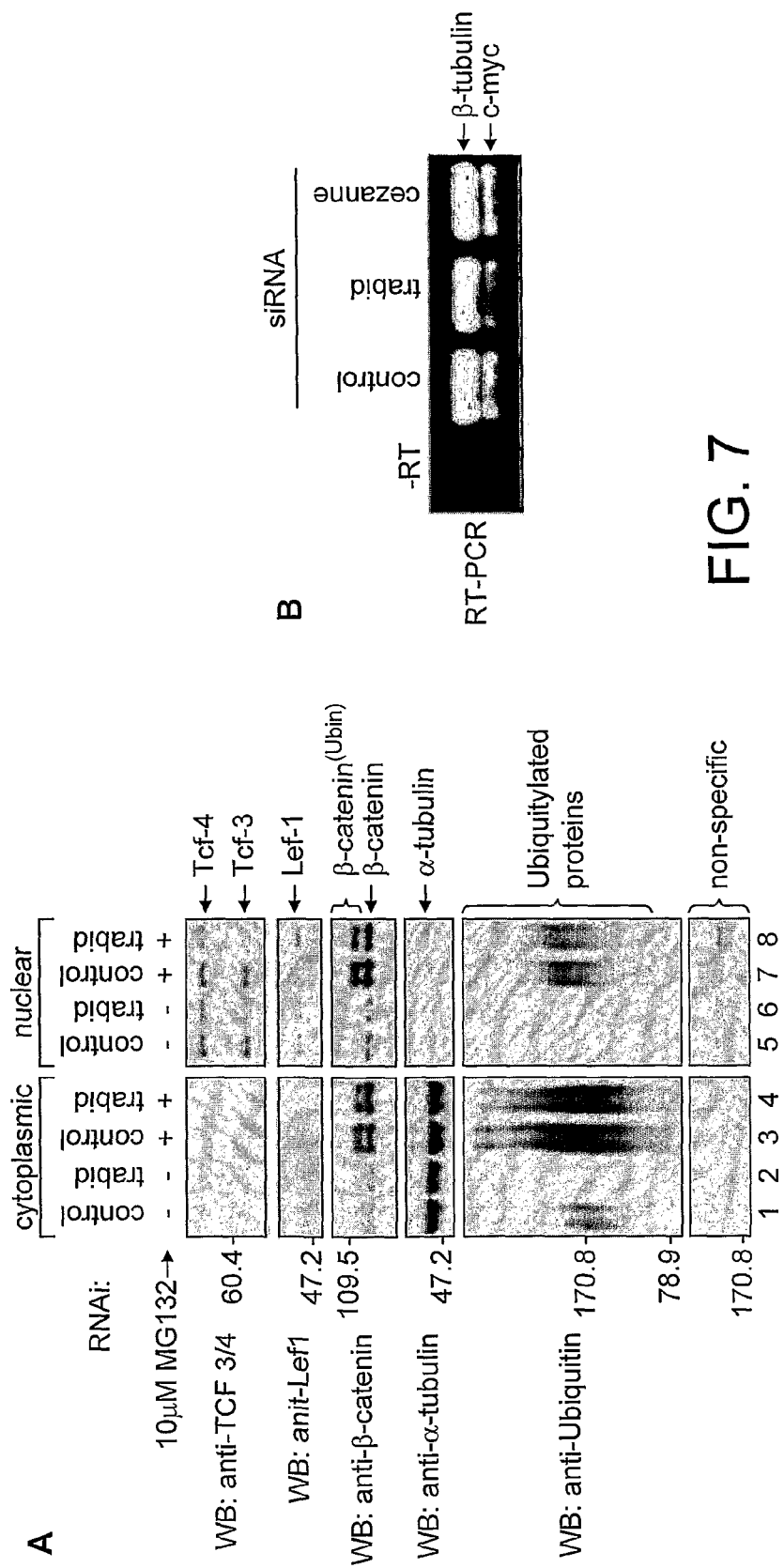
FIG. 7 shows photographs.

FIG. 7 shows the effect of Trabid depletion on cellular levels of Wnt pathway components and Wnt target genes in mammalian cells (in this example 293T cells).

FIG. 7(A) shows a significant reduction in the levels of TCF transcription factors 3 and 4 (but not Lef1) were observed in the nuclear fractions of Trabid depleted cells.

It is further demonstrated that Trabid has E3 ubiquitin ligase activity. Evidence for this is presented in FIG. 7. In particular, the less ubiquitylated beta-catenin and less ubiquitylated global protein after Trabid depletion in FIG. 7A evidence this activity. Inhibition or reduction of this activity is useful for reduction of Wnt pathway activity. This activity is likely mediated by the NZF finger region of Trabid.

Prominent ubiquitylated species of β-catenin is detectable upon proteasome inhibition (MG132, lanes 3 and 7), but is less pronounced in Trabid-depleted cells (lanes 4 and 8). A reduction in global ubiquitylated proteins is observed (antiubiquitin). FIG. 7(B) shows that expression of c-MYC, a TCF target gene, is down-regulated in Trabid-depleted cells. Thus the invention relates to the downregulation of c-MYC by reduction of Trabid activity.

SUMMARY

We have identified Trabid as a deubiquitylating enzyme (and E3 ubiquitin ligase), that is required for the full response to Wnt pathway stimulation and TCF-dependent transcription in mammalian cells. The evidence points to a nuclear role for Trabid, such as a regulator of TCF-3/4 expression. The reduced levels of TCF-3/4 in Trabid-depleted cells may be the rate-limiting factor that could account for the suppression of Wnt pathway activation, even when a stabilised form of β-catenin is used (FIG. 6C). Trabid may also be required for the efficient ubiquitylation of β-catenin (FIG. 7A). Thus, regulated turnover of nuclear β-catenin may be important for continuous TCF transcription. The activity of deubiquitylating enzymes is important for TCF transcription. We have identified Trabid as such an enzyme that can regulate levels of Wnt pathway-specific proteins, and thus directly affect TCF-dependent transcription. We demonstrate modulation of Trabid in the modulation of TCF-dependent transcription/Wnt signalling.

Example 13

The OTU domain of Cezanne was one of two isolates in a yeast two-hybrid screen with the armadillo repeat domain of APC as a bait that were specific for the wild-type (WT) domain, but did not bind to a mutant version of it. This WT-specific association was confirmed by co-immunoprecipitation of comparable protein fragments in mammalian and Drosophila cells. Subsequent RNA interference (RNAi) experiments revealed that the depletion of Trabid, but not of Cezanne, affected the TCF-mediated transcription in mammalian cells (see below). Therefore, we focused our further analysis on Trabid.

Trabid Preferentially Cleaves K63-linked Ubiquitin in vitro

Figure 8:
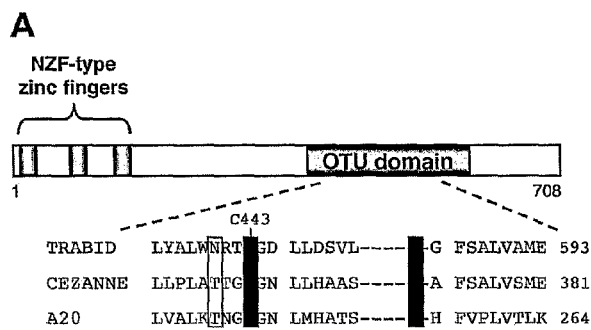
FIG. 8. Trabid is a DUB with a preference for K63-linked ubiquitin
(A) Domains of human Trabid, and alignment of the invariant cysteines and histidines (shaded in black) of three human OTU family members (the catalytically-dead C443S substitution is indicated); note the active site aspartate (boxed) found in most OTU proteins, but substituted by alanine in Trabid family members. (B) DUB assays, with WT and mutant HA-tagged Trabid immunoprecipitated from transfected 293T cells, as indicated, incubated with K48- or K63-linked ubiquitin (UB2-7); asterisk indicates ubiquitylated protein co-immunoprecipitated with the catalytically-dead C443S. (C) in vitro DUB assays, with WT and mutant GST-tagged C- or N-terminal fragments of Trabid expressed in bacteria (left; see also FIG. 9B), incubated with K63-linked ubiquitin (UB2-7; right); Ub-A1, ubiquitin aldehyde.
Figure 8:
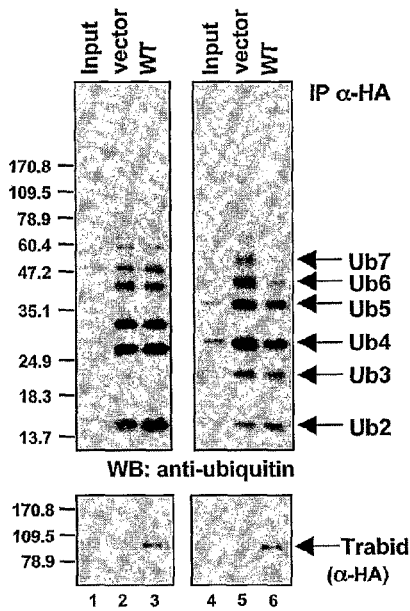
Figure 8:
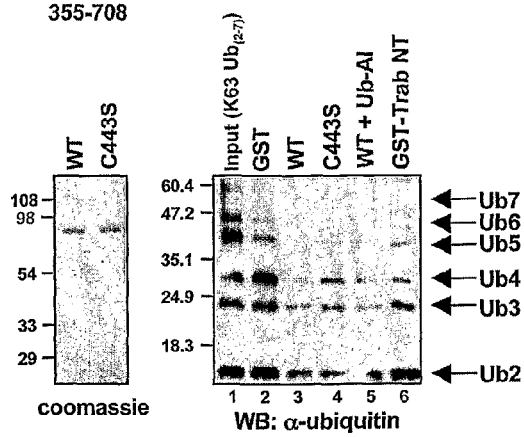

Trabid is 708 amino acid residues in length and contains an OTU domain in its C-terminus, and three NZF-type zinc fingers in its N-terminus (FIG. 8A). The latter are a defining feature of Trabid orthologs, which are also distinguishable from other OTU family members by their conserved D>A substitution in the putative catalytic pocket of their OTU domain (FIG. 8A, boxed). Indeed, the substituted aspartate residue is part of the catalytic Asp Cys His triad (FIG. 8A) commonly found in the active site of cysteine proteases, and critical for their function. This raises the question whether the variant OTU domain of Trabid orthologs does in fact have DUB activity.

Ubiquitin Cleavage Assays

To test this, we immunoprecipitated hemagglutinin (HA)-tagged Trabid from transfected 293T cells and incubated this in vitro with synthetic polyubiquitin (chains consisting of 2-7 ubiquitin monomers, Ub2-Ub7) linked via K48 or K63 of ubiquitin. Indeed, HA-Trabid was able to cleave K63-linked ubiquitin although the activity was predominantly directed towards the longer chains in the mixture (Ub6, Ub7; FIG. 8B, lane 8). In contrast, there was no detectable DUB activity of HA-Trabid on K48-linked ubiquitin chains (FIG. 8B, lanes 2-5). As expected, substitution of the catalytic cysteine 443 to serine in the OTU domain (C443S) blocked the DUB activity of HA-Trabid (FIG. 8B, lane 10). Interestingly, alanine substitutions of the first invariant cysteine in each of the three NZF fingers (3×ZnF), or in the third finger only (C155A), also blocked this activity (FIG. 8B, lane 9; FIG. 15). This was not due to reduced expression levels of these mutants (FIG. 8B, lower panel; FIG. 15). This implicates not only the OTU domain of Trabid in its DUB activity in vivo, but also its NZF motifs (see below).

To exclude the possibility that the observed DUB activity was due to other proteins co-precipitating with HA-Trabid, we conducted in vitro DUB assays with bacterially expressed glutathione-S-transferase (GST)-tagged C-terminus of Trabid (GST-Trabid CT, amino acids 355-708) (FIG. 8C, left panel). Indeed, WT GST-Trabid CT, but not its C443S mutant version, displayed DUB activity on K63-linked ubiquitin chains (FIG. 8C, lanes 3, 4), similarly to immunoprecipitated HA-Trabid (FIG. 8B). Moreover, pre-incubation of WT GST-Trabid CT with ubiquitin aldehyde, a specific inhibitor of DUB enzymes, blocked its DUB activity (FIG. 8B, lane 5). Evidently, the NZF fingers of Trabid are not essential for the in vitro DUB activity of the bacterially expressed protein, possibly because this assay involves relatively high protein concentrations. Indeed, the NZF fingers of Trabid themselves do not possess DUB activity since a bacterially expressed protein fragment spanning the N-terminus of Trabid (GST-Trabid NT, amino acids 1-354) was inactive in the DUB assay (FIG. 8B, lane 6). We conclude that the OTU domain of Trabid possesses DUB activity with a preference for K63-linked ubiquitin.

Trabid Preferentially Binds to K63-linked Ubiquitin Chains in vitro

Figure 9:
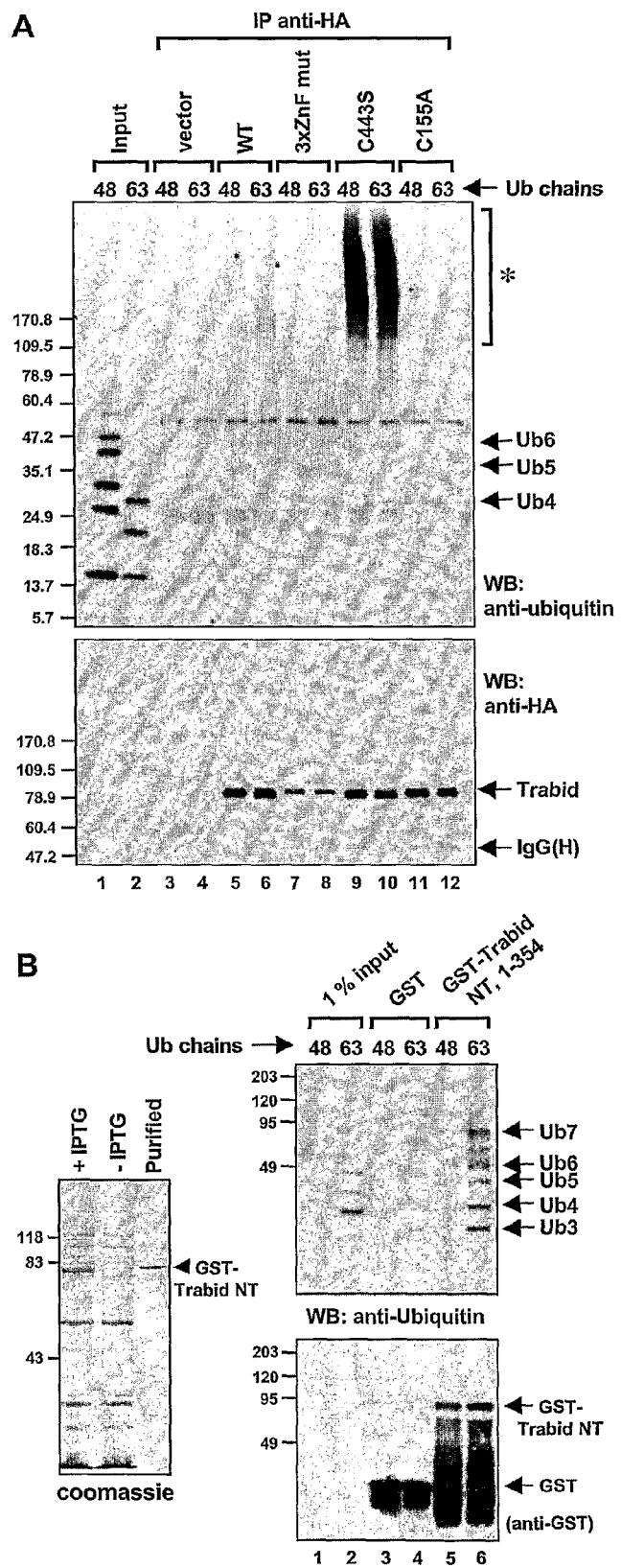
FIG. 9. Preferential binding of Trabid to K63-linked ubiquitin via its NZF motifs
A) Ubiquitin binding assays, with WT and mutant HA-Trabid immunoprecipitated from transfected 293T cells, and incubated in vitro with K48- or K63-linked ubiquitin (UB2-7); asterisk indicates ubiquitylated protein co-immunoprecipitated with WT and C443S (see also FIG. 8B). (B) Pull-down assays, with a GST-tagged N-terminal fragment of Trabid (see also FIG. 8C) expressed in bacteria (left), and incubated with K48- or K63-linked ubiquitin; note the strong binding preference for K63-linked chains (lanes 5 and 6).

The N-terminal zinc fingers of Trabid are clearly related to the ubiquitin-binding NZF motifs found in the TAB2 and TAB3 adaptor proteins of the TAK1 kinase complex (Kanayama et al., 2004) (FIG. 16). To test whether Trabid binds to ubiquitin, we conducted in vitro pull-down assays by incubating synthetic ubiquitin chains with WT or mutant HA-Trabid immunoprecipitated from transfected 293T cells. This revealed that WT HA-Trabid specifically bound to K63-linked but not to K48-linked Ub4-Ub6 (FIG. 9A, arrows; note that Ub4, Ub5 and Ub6 were highly enriched in the precipitate compared to the input; FIG. 9A, lanes 2 and 6). Significantly less binding was observed with the 3×ZnF and C155A mutants (FIG. 9A, lane 8, 12). In contrast, the C443S mutant showed at least as much binding to K63-linked ubiquitin as the WT (FIG. 9A, lane 10). Thus, the NZF fingers of Trabid are ubiquitin-binding motifs that show a strong preference for K63-linked ubiquitin, while the OTU domain is not required for this binding.

In support of this, C443S, but neither of the NZF mutants, co-precipitated an abundance of endogenous ubiquitylated proteins from 293T cell lysates (FIG. 9A, lanes 9 and 10, asterisk; see also FIG. 8B, lanes 5 and 10) that are also detectable, albeit to a lesser extent, in the WT precipitates (FIG. 9A, lanes 5 and 6). These are likely to represent ubiquitylated substrates bound to the NZF fingers of WT HA-Trabid, and trapped by the catalytically inactive OTU domain of the C443S mutant.

Finally, we used an in vitro GST pull-down assay to show that GST-Trabid NT has a strong preference for binding to K63-linked over K48-linked ubiquitin (FIG. 9B), indicating that this fragment contains a domain binding to K63-linked ubiquitin, most probably the NZF motifs. Based on this, and on the observed loss of DUB activity of the NZF mutants (FIG. 8B; FIG. 15B), we conclude that the NZF-mediated binding of Trabid to K63-linked ubiquitin is necessary for its efficient DUB activity in vivo.

Trabid is Required for TCF-dependent Transcription

We used RNAi in different human cell lines to examine the roles of endogenous Trabid and Cezanne in Wnt signaling. We generated an antiserum against the N-terminus of Trabid, to establish that Trabid is expressed in 293 cells, both in the cytoplasmic and nuclear fractions (FIG. 17A). Consistent with this, exogenous HA-Trabid is also found in both cytoplasm and nucleus of these cells, and of 293T cells (FIGS. 17B, C). Indeed, in the colorectal cancer cell line SW480 (whose Wnt pathway is active due to mutational inactivation of APC;), we observed overexpressed HA-Trabid largely in the nucleus (FIG. 17D).

Next, we used 293T cells transfected with HA-Trabid or HA-Cezanne, to test the specificity of two different siRNAs, and to optimize their efficiency of depletion (FIG. 18). We further confirmed that the Trabid-specific siRNA, but not the Cezanne-specific siRNA, reduced the level of endogenous Trabid transcripts in these cells to virtually undetectable levels (as judged by semi-quantitative RT-PCR; FIG. 18A), and that of endogenous Trabid protein to <50% (FIG. 10A).

To see whether Trabid is required for the transcription of endogenous TCF target genes in Wnt-stimulated cells, we measured the expression levels of two well-established transcriptional targets of Wnt signaling, c-MYC and AXIN2, by using quantitative RT-PCR. We first confirmed that the transcript levels of c-MYC and AXIN2 were induced >2× in 293 cells transfected with a control siRNA exposure to Wnt3A (FIGS. 10B, C). We also found that the levels of the recently discovered Wnt signaling factor BCL9 was >2× induced under these conditions (FIG. 10B); However, the Wnt-induced stimulation of all three Wnt target genes was completely blocked in Trabid-depleted 293 cells (FIGS. 10B, C; note also the efficient depletion of Trabid transcripts). Trabid depletion also reduced the expression of these Wnt target genes to ~50% in unstimulated 293 cells (FIGS. 10B, C), perhaps reflecting a low constitutive level of Wnt pathway activity in these cells. Thus, Trabid is required for the transcription of endogenous TCF target genes in response to Wnt stimulation. Moreover, we demonstrate that reduction of Trabid activity reduces Wnt signalling in human cells.

Next, we depleted Trabid in SW480 colorectal cancer cells, and we monitored the effects of this by using the TOPFLASH assay (based on a luciferase reporter linked to multiple TCF binding sites) as a specific and quantitative read-out of Wnt pathway activity (Korinek et al., 1997 Science Vol. 275 pp 1784-1787). SW480 cells were transfected with control siRNA, or with Cezanne- or Trabid specific siRNAs, and subsequently with the TOPFLASH reporter and an internal control (CMV-renilla). We found that depletion of Trabid reduced the TOPFLASH activity to ~40% of the normal levels of SW480 cells, whereas Cezanne depletion had no effect (FIG. 10D). The activity of a luciferase reporter containing mutated TCF binding sites (FOPFLASH) was unaffected (FIG. 10D). We also asked whether Trabid overexpression would affect TCF-mediated transcription. A modest, but significant, increase in TOPFLASH activity was observed in control siRNA cells co-transfected with WT HA-Trabid (FIG. 10D, lanes 1 and 7), but neither with C155A nor with C443S (FIG. 10D, lanes 8 and 9). Taken together, these results indicate that Trabid but not Cezanne is a positive regulator of TCF-mediated transcription in these colorectal cancer cells.

NF-κB Signaling

Given the strong functional link of Trabid relatives to NF-κB signaling, we also tested whether NF-κB-dependent transcription is sensitive to Trabid depletion. We transfected 293T cells with a luciferase reporter containing multiple NF-κB binding sites, and stimulated these cells by co-transfection of the TNF receptor IT (TNFR-II), which resulted in a ~7× increase of NF-κB-dependent transcription compared to the vector control (FIG. 10E, lanes 1 and 4). This activity was unaffected in Trabid-depleted cells (FIG. 10E, lanes 4 and 10). Further controls in this experiment included co-transfection with a dominant negative IκB (IκB-DN) protein that effectively blocked the TNFR-II induction, and with Wnt3A, which did not affect this NF-κB reporter assay (FIG. 10E). Thus, Trabid is not required for NF-κB-mediated transcription, consistent with the previous conclusions based on Trabid overexpression.

Ubiquitin Binding and DUB Activities of Trabid are Important for its Function in TCF-dependent Transcription To rule out off-target effects of Trabid siRNAs, we conducted rescue experiments with re-expressed Trabid. We introduced silent mutations into WT and mutant HA-Trabid rescue constructs that rendered these refractory to RNAi-mediated depletion (FIG. 18C). We then tested these constructs for their rescue activity in Trabid-depleted SW480 cells, and found that the WT HA-Trabid construct restored TOPFLASH activity to ~70% of the level of control-transfected cells (FIG. 10D, lanes 1, 3 and 10); Importantly, neither C443S nor C155A were able to restore TOPFLASH transcription in Trabid-depleted cells (FIG. 10D, lanes 3, 11 and 12), despite being expressed at similar levels to the WT (FIG. 10D, lower panel). Similar results were observed in Wnt3A-stimulated 293 cells (FIG. 19). Taken together, these results indicate that the ubiquitin binding and DUB activities of Trabid are required for its function during TCF-mediated transcription in human cells with elevated Wnt pathway activity.

Epistasis Analysis Indicates that Trabid Acts Below the Stabilization of β-catenin We conducted epistasis experiments, based on TOPFLASH assays in Trabid-depleted 293 cells, to identify the level within the Wnt signaling cascade at which Trabid acts. First, we examined cells transfected with a plasmid encoding Wnt3A, which stimulates the TOPFLASH activity ~6× over the vector control (FIG. 18A; note that β-catenin accumulates under these conditions (FIG. 18A, lower panel, lanes 1 and 2). In cells transfected with Trabid siRNAs, the Wnt3A-induced stabilization of β-catenin was unaffected, but the TOPFLASH activity was reduced to ~30% of the level in control cells (FIG. 18A, lanes 2 and 4). This suggests that Trabid acts downstream in the Wnt pathway, below the stabilization of β-catenin.

Given its role in ubiquitin conjugation, we also asked whether the activity of β-TrCP might be affected by Trabid depletion. We used a dominant-negative form of mouse β-TrCP (β-TrCPΔF) that binds to β-catenin but not to the SCF complex, and expressed this in 293T cells, which causes a high level of Wnt pathway activity in a dose-dependent manner: TOPFLASH activity was stimulated ~6× and 10× over the vector control with 200 and 400 ng of transfected construct, respectively (FIG. 18B, lanes 1 to 3). However, in Trabid-depleted cells, stimulation of TOPFLASH with the same amount of transfected β-TrCPΔF was reduced significantly (to ~40-50% of controls; FIG. 18B, lanes 5 and 6), although the levels of β-TrCPΔF were unaffected (FIG. 18B, lower panel). We also found that the stabilization of β-catenin as a result of Dishevelled overexpression, or of inhibition of GSK3 β by LiCl, was unaffected by Trabid depletion, whereas the TOPFLASH transcription due to these stimuli was reduced to <50% (FIG. 20). We conclude that Trabid acts to control the transcriptional activity of β-catenin rather than its stabilization.

Figure 11:
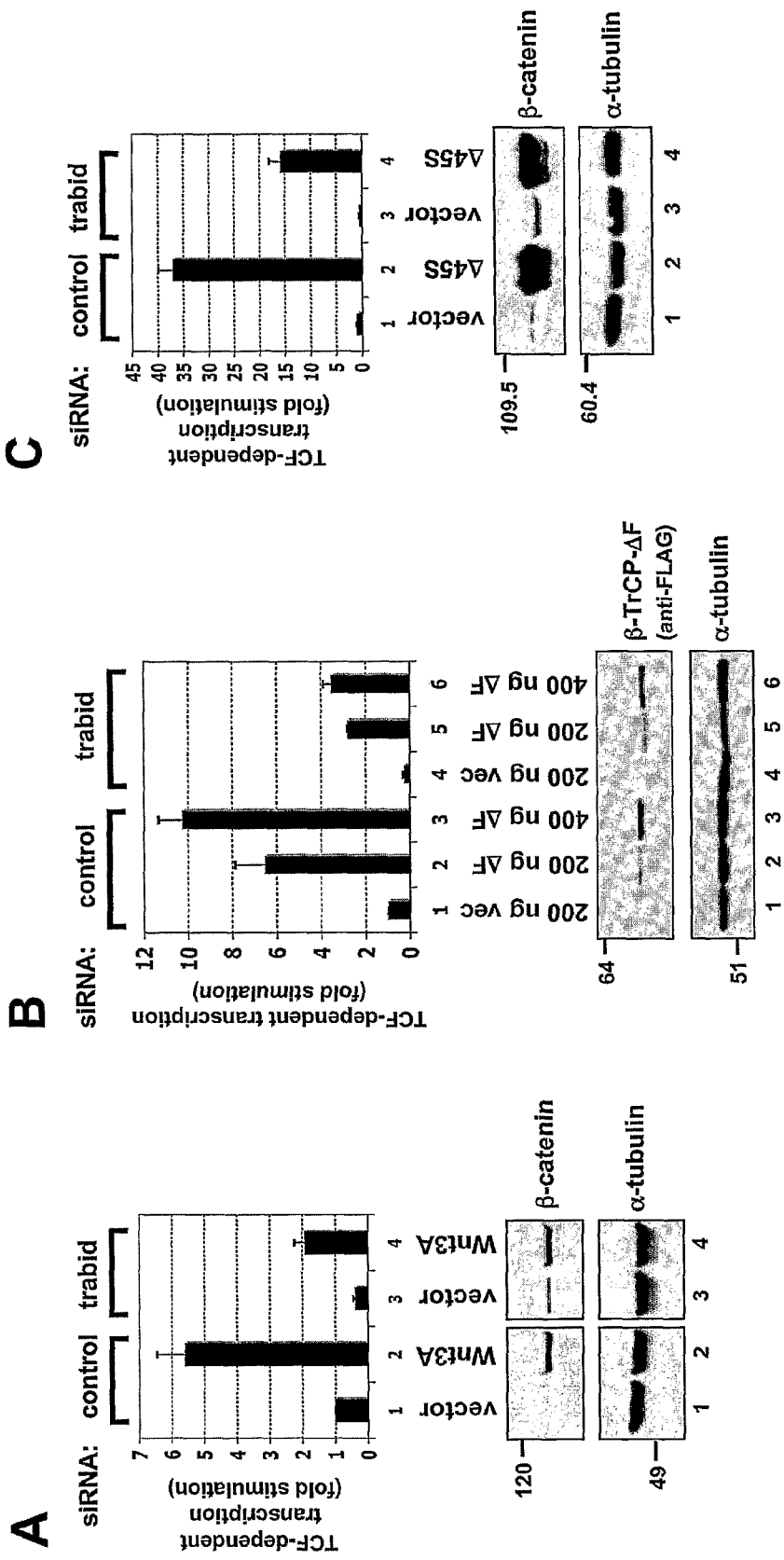
FIG. 11. Epistasis experiments indicate a nuclear function of Trabid

To demonstrate this directly, we transfected 293T cells with an activated form of β-catenin, β-catenin Δ45S (Δ45S) (Morin et al., 1997 Science Vol 275 pp 1787-1790), which is refractory to phosphorylation, and thus a potent stimulator of TOPFLASH activity (~35× over the vector control; FIG. 11C, lanes 1 and 2). However, in Trabid-depleted cells the TOPFLASH stimulation was reduced to 40% (FIG. 11C, lanes 2 and 4). Consistent with this, we found that Trabid depletion in HCT-116 colorectal cancer cells (that harbor the same Δ45S mutation (Morin et al., 1997 ibid)) resulted in a ~50% reduction of their TOPFLASH activity compared to control cells (FIG. 21). This corroborates our conclusion that Trabid is required for the transcriptional activity of β-catenin.

Trabid Affects the Levels of Nuclear β-catenin, TCF-4 and TCF-3

We next asked whether depletion of Trabid affected the stability, or the ubiquitylated status, of potential nuclear targets in the Wnt pathway. We thus depleted Trabid in 293T cells whose Wnt pathway was stimulated by LiCl treatment, and we prepared cytoplasmic and nuclear fractions of these cells, to evaluate the effects of Trabid depletion specifically on the nuclear proteins.

We first examined the β-catenin levels, but the only consistent change we found was a small decrease of the nuclear β-catenin levels in Trabid-depleted cells, especially in LiCl-stimulated cells (FIGS. 12A, C, lanes 11 and 12) while the cytoplasmic β-catenin levels, if anything, appeared slightly increased in these cells (FIG. 12A; see also FIG. 11A). A similar effect was also apparent in nuclear exacts prepared from Trabid-depleted 293 cells (FIG. 12B). To examine the ubiquitylation of β-catenin in Trabid-depleted cells, we treated 293T cells with the proteasome inhibitor MG132, which results in the appearance of higher-molecular weight species, corresponding to ubiquitylated forms of β-catenin (FIGS. 12A, C, brackets); However, there was no increase of ubiquitylated β-catenin in MG132-treated cells after Trabid depletion (FIGS. 12A, C); if anything, a small decrease of ubiquitylated β-catenin was detectable in the Trabid-depleted cytoplasmic fractions (FIG. 12A, lanes 3 and 4). Thus, while Trabid may affect the nuclear retention of β-catenin somewhat, it is not required for its ubiquitylation, consistent with our conclusion that Trabid does not affect the degradation of β-catenin.

We also examined the levels of TCF factors in Trabid-depleted cells. This revealed a small but consistent reduction of the nuclear levels of TCF3 and TCF4 in Trabid-depleted 293T cells (FIG. 12A, lanes 7 and 8), visible also after LiCl and MG132 treatment (FIG. 12A, lanes 9-12). A similar reduction of the nuclear TCF4 levels was also detectable in Trabid-depleted 293 cells (FIG. 12B). In contrast, the nuclear levels of LEF1, a member of the TCF family expressed at low levels in these cells, were not sensitive to Trabid depletion (FIGS. 12A, B), nor were those of the β-catenin-binding protein Parafibromin (FIGS. 12A, B). None of these transcription factors showed any modification in response to MG132, indicating that they are not ubiquitylated. Thus, the main effect of Trabid depletion was a mild but selective decrease of the protein levels of TCF3 and TCF4, the predominant TCF factors in these human embryonic kidney cell lines.

We also examined whether Trabid depletion might affect the interaction between TCF and β-catenin. We thus immunoprecipitated TCF4 from nuclear extracts of 293T cells, and detected co-precipitation of β-catenin in lysates from control and Trabid-depleted cells by Western blot analysis. However, although the levels of TCF4 and β-catenin were reduced after Trabid depletion (see above), there was no detectable-change in the levels of TCF4-associated β-catenin (FIG. 12C, lanes 7-12). We conclude that Trabid is not essential for the association of β-catenin with TCF4 in these cells.

Direct Linkage of Transactivation Domains from VP16 or β-catenin to LEF1 Bypasses the Need for Trabid The observed reductions of nuclear β-catenin and TCF levels in Trabid depleted cells might explain why the TCF-mediated transcription is reduced under these conditions. However, this is unlikely since overexpression of activated β-catenin, or of TCF factors, does not restore normal levels of TOPFLASH activity in Trabid-depleted cells; the levels of these proteins are not detectably reduced after overexpression (FIG. 11C), arguing that Trabid primarily regulates their function in transcription, rather than their levels.

One possibility is that Trabid affects the recruitment of co-activators to the C-terminus of TCF-associated β-catenin, itself a potent transactivation domain (TAD). If so, then linkage of a TAD to TCF might bypass the requirement for Trabid in TCF-mediated transcription. We thus tested a chimera (catC-LEF1Δ56; (Hsu et al., 1998 Mol. Cell. Biol. vol. 18-pp 4807-4818)) in which the C-terminus of β-catenin was directly fused to LEF1 lacking its N-terminal 56 residues (required for β-catenin binding), which mediates strong dose-dependent transactivation of TOPFLASH in transfected 293 cells (FIG. 13, lanes 1-3). We also tested a similarly active chimera between the TAD from the viral protein VP16 and LEF1 without its N-terminus (VP16-LEF1ΔN; (Ishitani et al., 2005 Nat. Cell. Biol. Vol. 7 pp 1106-1112)) (FIG. 13, lanes 4 and 5). Interestingly, catC-LEF1Δ56 was only very slightly dependent on Trabid for transactivation (FIG. 13, lanes 7 and 8), significantly less so than Δ45S (FIG. 11C). Furthermore, VP16-LEF1ΔN was not dependent on Trabid at all, showing essentially the same dose-dependent transactivation of TOPFLASH irrespective of Trabid depletion (FIG. 13, lanes 9 and 10). This argues that Trabid acts to control co-activator recruitment to the TCF-β-catenin complex.

*Drosophila* Trabid is a Positive Regulator of the Wingless Response

As mentioned in the Introduction, *Drosophila* possesses a single Trabid orthologue (dTrabid) with a typical Trabid signature (FIG. 8A; FIG. 16). We asked whether loss of dtrabid also affected Wnt signaling in *Drosophila*, by deleting dtrabid by homologous recombination. To our surprise, dTrabid null mutants were viable and fertile, which suggests that dtrabid may function redundantly with another gene.

We thus tested the function of dTrabid in a more sensitive assay, by asking whether lowering the dose of Trabid by half (in dTrabid heterozygotes) would affect the rough eye phenotype caused by expression of Wingless in the eye imaginal disc (FIGS. 14A, B). This was indeed the case: dTrabid heterozygosity suppressed this phenotype (FIG. 14C, compare to B), similarly to dTCF heterozygosity (FIG. 14D). Furthermore, dTrabid heterozygosity also suppressed the rough eye phenotype due to overexpression of Armadillo (the β-catenin of *Drosophila*) to some extent (FIG. 14F, compare to E). In contrast, we observed no genetic interactions between dtrabid and components of EGF receptor signalling, a pathway that controls differentiation in the developing fly eye: for example, the rough eye phenotype due to overexpression of Argos, an inhibitor of this pathway, remained unchanged in dtrabid heterozygotes (FIGS. 14G, H), as was that due to Rhomboid overexpression, an activator of this pathway. Likewise, the rough eye phenotypes due to Notch pathway perturbations (Notch heterozygosity, or overexpression of Delta) were also unaffected in dtrabid heterozygotes. These results implicate dTrabid as a positive regulator of the Wingless response in *Drosophila*, consistent with our results in human cell lines. Furthermore, they suggest that dTrabid does not have wide-spread effects on other signalling pathways. Thus, it is an advantage of the invention that side effects of Trabid modulation are few.

Methods for Example 13

Plasmids and Antibodies pHM6-HA-Trabid and pHM6-HA-Cezanne (Evans et al., 2003; Evans et al., 2001) were kindly provided by Dr. Paul Evans; point mutants were created using QuickChange (Stratagene), and confirmed by DNA sequencing. For GST-Trabid constructs, PCR-amplified Trabid cDNA fragments were cloned between EcoRI and XhoI of the bacterial expression vector pGEX-6P-1. The following antibodies used were: α-TCF4, α-TCF3/4 and α-Ubiquitin (Upstate), α-β-catenin and α-FLAG M2 (Sigma), α-Parafibromin (Bethyl Laboratories), α-HA 3F10 (Roche), α-LEF1 and α-TLE (Santa Cruz), α-α-tubulin (Abcam). Polyclonal antibodies to Trabid were generated (Eurogentec) by immunizing rats with an N-terminal fragment of Trabid (amino acids 1-354) fused to GST and purified from bacteria. The crude rat α-Trabid serum was used at 1:100 dilution for Western-blotting.

Cells, Transfections and Treatments

HEK293, HEK293T, SW480 and HCT-116 cells were maintained in Dulbecco's modified Eagle's medium supplemented with 10% fetal bovine serum. Small interfering RNA (siRNA, Dharmacon) duplexes used to target Trabid and Cezanne mRNAs are as follows (only sense strand shown): Trabid #1, AGA GGC UUC UUC AAU AAU AdTdT; Trabid #2, AGA GGU GUC UCA ACA AGC AdTdT; Cezanne #1, GAA UCU AUC UGC CUU UGG AdTdT; Cezanne #2, AGA CTU CCG CAG CUU CAU AdTdT. The negative control siRNA was purchased from Ambion (Catalog No. AM4611). Transfection of siRNA duplexes and plasmid DNA was performed using Lipofectamine 2000 (Invitrogen Life Technologies).

TOPFLASH and NF-κB Reporter Assays

Cells were seeded in 12-well plates at a density of $0.8 \times 10^5$ cells per ml and allowed to attach to the dish surface for 12-16 hrs before transfection. For RNAi experiments, cells were first transfected with siRNAs (100 nM final concentration) and, after 24 hrs, re-transfected with 250 ng of pTOPFLASH or pFOPFLASH, 20 ng of pRL-CMV (renilla luciferase internal control) and 1.0 □g of the effector plasmid DNA, unless specified otherwise. For NF-κB assays, cells were transfected with a luciferase reporter containing 4× NF-κB binding sites (Clontech) and where indicated, pEAK12-HA-TNFRII and pEAK12-IκB□DN (S32A, S36A). Total amounts of DNA per transfection were equalized with empty vector. After a further 24 hrs, cells were harvested and lyzed in passive lysis buffer (Dual Luciferase Reporter Assay System; Promega). Protein concentration was determined with a Coomassie based reagent (Pierce); 10 □g of total protein were used per sample (for TOPFLASH assays, or Western blotting). For each transcription assay, the relative luciferase activity from control cells was set arbitrarily to 1, and the values from experimental assays were expressed as fold induction over the control.

Immunoprecipitations and GST Pull-down Assays

Adherent cells were washed twice with PBS and incubated in NP40 lysis buffer (50 mM Tris-HCl, pH 7.4, 120 mM NaCl, 1% NP-40, 1 mM EDTA, 5 mM $Na_3VO_4$, 5 mM NaF, 0.5 μg/ml aprotinin, 1 μg/ml leupeptin) on ice for 10 min. Cells were collected by scraping and centrifuged at 14,000 rpm for 10 min (4° C.). Immunoprecipitations were performed using 500 to 700 μg of cell extracts pre-cleared with a 50% solution of protein G-Sepharose beads (100 μL, Zymed), before incubation with 4 μg of the indicated antibody for 2 h at 4° C. Antibody-antigen complexes were captured with 100 μL of 50% protein G beads for 1 h at 4° C. GST pull-down assays were performed with 1 μg of bacterially expressed GST or GST-Trabid coupled to a 50% solution of glutathione-Sepharose 4B beads (50 μL, Amersham) and incubated with 500 to 700 μg of cell extracts as described above, or with K48- or K63-linked ubiquitin chains ($Ub_{2-7}$, Affiniti). Precipitated proteins were resolved by SDS-PAGE and analyzed by Western blotting. Nuclear and cytoplasmic fractions were prepared as described (Caruccio and Banerjee, 1999).

DUB assays

Assays were performed as described (Wang et al., 2004), with modifications. GST-Trabid constructs (1 μg) were incubated with 0.5 μg of synthetic ubiquitin chains, as above, in 20 μl buffer (150 mM KCl, 50 mM Hepes, pH 7.4, 10 mM DTT, 5% glycerol, 0.01% Triton X-100) for 60 min at 37° C. Reactions were terminated with 2× SDS-PAGE sample buffer, resolved by SDS-PAGE and analyzed by Western blotting. Glutathione S-transferase (GST) and GST-Trabid proteins were expressed in *Escherichia coli* BL21 (DE3) and purified using glutathione-Sepharose beads (Amersham) according to the supplier's instructions. Ubiquitin aldehyde was purchased from Calbiochem.

Real-time Quantitative RT-PCR 293 cells were grown in 12-well plates, transfected with siRNAs and, after for 24 hrs, incubated with Wnt3A-conditioned (from mouse L cells stably expressing Wnt3A) or control medium (from mouse L cells) for a further 6 hrs. Cells were harvested in ice-cold PBS and used directly for cDNA synthesis with the Superscript III kit as instructed (Invitrogen). Duplicate cDNA samples were amplified with the TaqMan Universal PCR Master Mix and gene-specific TaqMan TAMRA probes in an ABI Prism 7900HT machine (Applied Biosystems). Standard curves were based on the housekeeping gene HPRT whose expression was not affected by W3a-CM treatment. Results are expressed as fractions of HPRT values.

Drosophila Crosses

A deletion of dTrabid (CG9448) was generated by homologous recombination (Gong and Golic, 2003; Rong and Golic, 2001). dTrabid/TM3 or y w control flies were crossed to sev-wg (Brunner et al., 1997), GMR.GAL4>UAS.Armadillo (Freeman and Bienz, 2001; Greaves et al., 1999), and grown at 25° C. Eyes of the resulting heterozygous progeny were scored as described (Freeman and Bienz, 2001). The strong dTCF[3] allele was used (van de Wetering et al., 1997).

All publications mentioned in the above specification are herein incorporated by reference. Various modifications and variations of the described methods and compositions of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

```
Informal Sequence Listing
siRNA (No. 1) to Trabid
AGA GGT GTC TCA ACA AGC A siRNA (No. 2) to Trabid
AGA GGC TTC TTC AAT AAT A siRNA Trabid #1,
AGA GGC UUC UUC AAU AAU AdTdT;

siRNA Trabid #2,
AGA GGU GUC UCA ACA AGC AdTdT;

siRNA Cezanne #1,
GAA UCU AUC UGC CUU UGG AdTdT;

siRNA Cezanne #2,
AGA CUU CCG CAG CUU CAU AdTdT
```

The invention claimed is:

1. A method of reducing TCF-mediated transcription, said method comprising contacting a cell with an siRNA specific for a human Trabid molecule that comprises an N-terminal finger motif, in an amount sufficient to inhibit TCF-mediated transcription, wherein the siRNA specific for the human Trabid molecule is an inhibitor of K63 linked ubiquitin binding activity of the human Trabid molecule.

2. The method according to claim 1 wherein said TCF transcription is Dvl-stimulated, Wnt3A stimulated, LiCl stimulated, loss or mutation of APC stimulated, activation or mutation of beta-catenin stimulated or mβ-TrCp-ΔF stimulated TCF transcription.

3. The method of claim 1, wherein said Trabid molecule is at least 40% identical to human Trabid.

4. A method of reducing Wnt-mediated signaling via inhibition of TCF-directed transcription, said method comprising contacting a cell with an siRNA specific for a human Trabid molecule that comprises an N-terminal NZF finger motif, in an amount sufficient to reduce Wnt-mediated signaling, wherein the siRNA specific for the human Trabid molecule is an inhibitor of K63 linked ubiquitin binding activity of the human Trabid molecule.

* * * * *